US009493543B2

(12) United States Patent
Bolt et al.

(10) Patent No.: US 9,493,543 B2
(45) Date of Patent: Nov. 15, 2016

(54) FACTOR VIII FUSION PROTEIN

(75) Inventors: Gert Bolt, Vaerloese (DK); Kristian Kjaergaard, Ballerup (DK); Peder Lisby Noerby, Birkeroed (DK); Ole Hvilsted Olsen, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/574,686

(22) PCT Filed: Feb. 10, 2011

(86) PCT No.: PCT/EP2011/051959
§ 371 (c)(1),
(2), (4) Date: Oct. 5, 2012

(87) PCT Pub. No.: WO2011/101284
PCT Pub. Date: Aug. 25, 2011

(65) Prior Publication Data
US 2013/0040889 A1  Feb. 14, 2013

Related U.S. Application Data

(60) Provisional application No. 61/306,177, filed on Feb. 19, 2010.

(30) Foreign Application Priority Data

Feb. 16, 2010 (EP) .................... 10153715

(51) Int. Cl.
*C07K 14/755* (2006.01)
*A61K 38/00* (2006.01)

(52) U.S. Cl.
CPC ............ *C07K 14/755* (2013.01); *A61K 38/00* (2013.01); *C07K 2319/00* (2013.01); *C07K 2319/30* (2013.01); *C07K 2319/31* (2013.01)

(58) Field of Classification Search
CPC ............ C07K 14/755; C07K 2319/00; C07K 2319/30; C07K 2319/31
See application file for complete search history.

(56) References Cited

U.S. PATENT DOCUMENTS

| | | | |
|---|---|---|---|
| 5,095,096 A | 3/1992 | Miki et al. | |
| 5,629,384 A | 5/1997 | Veronese et al. | |
| 5,843,440 A | 12/1998 | Pouletty et al. | |
| 5,932,462 A | 8/1999 | Harris et al. | |
| 6,524,572 B1 | 2/2003 | Li | |
| 2004/0076629 A1 | 4/2004 | Ceriani et al. | |
| 2005/0260194 A1 | 11/2005 | Peters et al. | |
| 2007/0106066 A1 | 5/2007 | Cherkasky | |
| 2007/0275873 A1 | 11/2007 | Heidner et al. | |
| 2008/0003218 A1 | 1/2008 | Lowman et al. | |
| 2008/0219978 A1* | 9/2008 | Ellsworth | 424/134.1 |
| 2008/0267949 A1 | 10/2008 | Revets et al. | |
| 2008/0292646 A1 | 11/2008 | Benhar et al. | |

| | | |
|---|---|---|
| 2009/0053790 A1 | 2/2009 | Fushikida et al. |

FOREIGN PATENT DOCUMENTS

| | | |
|---|---|---|
| CN | 101379077 A | 3/2009 |
| EA | 005404 B1 | 2/2005 |
| EP | 319315 A2 | 6/1989 |
| JP | 2004141173 A | 5/2004 |
| WO | 03/031464 A2 | 4/2003 |
| WO | 2004/062619 A2 | 7/2004 |
| WO | 2006/102652 A2 | 9/2006 |
| WO | 2007/056191 | 5/2007 |
| WO | 2007065691 A2 | 6/2007 |
| WO | 2008/025856 A2 | 3/2008 |
| WO | 2008/077616 A1 | 7/2008 |
| WO | WO 2008077616 A1 * | 7/2008 |
| WO | 2009/053368 A1 | 4/2009 |
| WO | 2009/108806 A1 | 9/2009 |
| WO | WO 2009108806 A1 * | 9/2009 |
| WO | 2009/156137 A1 | 12/2009 |

OTHER PUBLICATIONS

Bouwens et al., "Factor VIII alters tubular organization and functional properties of von Willebrand factor stored in Weibel-Palade bodies," Blood 118:5947-5956 (2011).*
Bouwens et al., "Factor VIII alters tubular organization and functional properties of von Willebrand factor stored in Weibel-Palade bodies," Blood 118:5947-5956 (2011 )—provided with OA mailed Oct. 4, 2013.*
Leyte et al., "Sulfation of Tyr1680 f Human Blood Coagulation Factor VIII is Essential for the Interaction of Factor VIII with von Willebrand Factor," J. Biol. Chem. 266:740-746 (1991).*
Dumont Jennifer et al, Blood, "Factor VIII-FC Fusion Protein Shows Extended Half-Life and Hemostatic Activity in Hemophilia A Dogs" [Abstract], 2009, vol. 114, No. 22, pp. 228.
Glabe et al, The Journal of Biological Chemistry, "Glycosylation of Ovalbumin Nascent Chains the Spatial Relationship Between Translation and Glycosylation", 1980, vol. 255, No. 19, pp. 9236-9242.
Julenius, Karin et al., Glycobiology, "Prediction, Conservation Analysis, and Structural Characterization of Mammalian Mucin-Type O-Glycosylation Sites", 2004, vol. 15, No. 2, pp. 153-164.
Kiely et al, Journal of Biological Chemistry, "Studies on the Attachment of Carbohydrate to Ovalbumin Nascent Chains in Hen Oviduct", 1976, vol. 251, No. 18, pp. 5490-5495.
Daeron, Marc, Annual Review of Immunology, "FC Receptor Biology", 1997, vol. 15, pp. 203-234.
Shen, Betty W. et al., Blood, "The Tertiary Structure and Domain Organization of Coagulation Factor VIII", 2008, vol. 111, No. 3, pp. 1240-1247.
Thim L, et al., Haemophilia, "Purification and Characterization of a New Recombinant Factor VIII(N8)", 2010, vol. 16, No. 2, pp. 349-359.
Authors: Fay J. P. et al., Title: Activation of factor VIII and mechanisms of cofactor action, Journal: Blood Reviews, Year: 2004, vol. 18, pp. 1-15.
Lenting, Peter J. et al., Life Cycle of Coagulation Factor VIII in View of Structure and Function, Blood, 1998, vol. 92, pp. 3983-3996.

* cited by examiner

*Primary Examiner* — Julie Ha
*Assistant Examiner* — Kristina M Hellman
(74) *Attorney, Agent, or Firm* — Nonna G. Akopyan

(57) ABSTRACT

The present invention relates to modified coagulation factors. In particular, the present invention relates to conjugated Factor VIII molecules fused to a polypeptide such as e.g. an antibody binding protein or a Fc domain.

19 Claims, No Drawings

FACTOR VIII FUSION PROTEIN

CROSS-REFERENCE TO RELATED APPLICATIONS

This application is a 35 U.S.C. §371 national stage application of International Patent Application PCT/EP2011/051959 (published as WO 2011/101284 A1), filed Feb. 10, 2011, which claimed priority of European Patent Application 10153715.7, filed Feb. 16, 2010; this application further claims priority under 35 U.S.C. §119 of U.S. Provisional Application 61/306,177, filed Feb. 19, 2010.

FIELD OF THE INVENTION

The present invention relates to modified coagulation factors. In particular, the present invention relates to Factor VIII molecules fused to a non-homologous polypeptide such as e.g. an antibody binding polypeptide, such as e.g. an Fc receptor or an Fc domain. The invention furthermore relates to use of such molecules as well as methods for producing such molecules.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jul. 19, 2012. The Sequence Listing is made up of 89,639 bytes, and the information contained in the attached "SEQUENCE LISTING" is identical to the information in the specification as originally filed. No new matter is added.

BACKGROUND OF THE INVENTION

Haemophilia A is an inherited bleeding disorder caused by deficiency or dysfunction of coagulation factor VIII (FVIII) activity. The clinical manifestation is not on primary haemostasis—formation of the blood clot occurs normally—but the clot is unstable due to a lack of secondary thrombin formation. The disease is treated by intravenously injection of coagulation factor FVIII which is either isolated from blood or produced recombinantly.

Current treatment recommendations are moving from traditional on-demand treatment towards prophylaxis. The circulatory half life of endogenous FVIII bound to von Willebrandt Factor is 12-14 hours and prophylactic treatment is thus to be performed several times a week in order to obtain a virtually symptom-free life for the patients. IV administration is for many, especially children and young persons, associated with significant inconvenience and/or pain.

Various methods have been employed in the development of a Factor VIII variant with significantly prolonged circulatory half life. A number of these methods relate to conjugation of Factor VIII with hydrohphilic polymers such as e.g. PEG (poly ethylene glycol).

There is thus a need in the art for novel Factor VIII products with factor VIII activity that comprise one or more of the following features: preferably homogenous in structure, preferably safe, preferably biologically degradable, and preferably have a significantly prolonged circulatory half life in order to reduce the number of factor VIII administration per week. There is likewise a need in the art for relatively simple methods for providing such molecules.

SUMMARY OF THE INVENTION

The present invention relates to a recombinant Factor VIII molecule, wherein said Factor VIII molecule is a fusion protein. The invention furthermore relates to methods for making such molecules as well as use of such molecules. Such molecules preferably have a modified circulatory half life.

DESCRIPTION OF THE INVENTION

Definitions

Fusion protein: Fusion proteins/chimeric proteins, are proteins created through the joining of two or more genes which originally coded for separate proteins. Translation of this fusion gene results in a single polypeptide with functional properties derived from each of the original proteins. Factor VIII molecules according to the present invention may be fused to another polypeptide. Preferably, the Factor VIII fusion protein will have a longer circulatory half life compared to the non-fused Factor VIII molecule.

A wide range of fusion partners can be joined to the FVIII part. These fusion partners can alter the properties of the fusion protein relative to wild-type FVIII by various mechanisms.

A number of fusion partners are presumed to delay in vivo clearance of FVIII by interaction with the neonatal Fc receptor (FcRn). Non-limiting examples of fusion partners that assumingly protracts FVIII by interaction with FcRn are immunoglobulin Fc domains, human serum albumin (hSA), and transferrin or parts of these proteins. Non-limiting examples of fusion proteins consisting of a FVIII part joined to polypeptides assumed to protract FVIII by interaction with FcRn are shown in Table 2. "Fc fusion derivatives" or "Fc fusion proteins" is herein meant to encompass FVIII variants according to the invention fused to an Fc domain that can be derived from any antibody isotype, although an IgG Fc domain will often be preferred due to the relatively long circulatory half life of IgG antibodies. The Fc domain may furthermore be modified in order to modulate certain effector functions such as e.g. complement binding and/or binding to certain Fc receptors. Fusion of a FVIII with an Fc domain, having the capacity to bind to FcRn receptors, will generally result in a prolonged circulatory half life of the fusion protein compared to the half life of the wt FVIII. Mutations in positions 234, 235 and 237 in an IgG Fc domain will generally result in reduced binding to the FcγRI receptor and possibly also the FcγRIIa and the FcγRIII receptors. These mutations do not alter binding to the FcRn receptor, which promotes a long circulatory half life by an endocytic recycling pathway. Preferably, a modified IgG Fc domain of a fusion protein according to the invention comprises one or more of the following mutations that will result in decreased affinity to certain Fc receptors (L234A, L235E, and G237A) and in reduced C1q-mediated complement fixation (A330S and P331S), respectively.

However, the present invention also includes FVIII variants fused to Fc domains having altered binding properties to e.g. the neonatal Fc receptors. If e.g. Fc domain variants have increased affinity to e.g. the neonatal Fc receptor, it is plausible that the in vivo circulatory half life of the fusion protein will be further improved. Examples of amino acid replacements in human IgG believed to modulate the affinity of the Fc domain to the neonatal Fc receptor are T250Q, M252Y, S254T, T256E, P257I, T307A, Q311I, and M428L (residue numbering according to the EU index).

Other fusion partners are presumed to delay in vivo clearance of FVIII by interaction with immunoglobulins. A non-limiting example of fusion partners that assumingly protracts FVIII by interaction with immunoglobulins is Fc receptors such as FcγRI (CD64) or FcRn or parts of these proteins. Non-limiting examples of fusion proteins consisting of a FVIII part joined to polypeptides assumed to protract FVIII by interaction with immunoglobulins are shown in Table 3.

Some fusion partners are presumed to delay in vivo clearance of FVIII by reducing the interaction with clearance receptors. A non-limiting example of fusion partners that assumingly protracts FVIII by reducing the interaction with clearance receptors is members of the low-density lipoprotein receptor family Fc receptors such as low-density lipoprotein receptor-related protein or parts of these proteins for instance for instance cluster of repeat 5 (CR5), 6 (CR6), and/or 7 (CR7). Non-limiting examples of fusion proteins consisting of a FVIII part joined to polypeptides assumed to protract FVIII by reducing the interaction with clearance receptors are shown in Table 4.

Other fusion partners are presumed to delay in vivo clearance of FVIII by interaction with platelets. A non-limiting example of fusion partners that assumingly protracts FVIII by interaction with platelets is single-chain (SC) antibodies binding to proteins on the platelet surface such as GPIIIa. In SC antibodies, the polypeptide sequence derived from immunoglobulin heavy chain can be situated N-terminal to the polypeptide sequence derived from immunoglobulin light chain. This order is referred to as HC-LC. The polypeptide sequence derived from immunoglobulin heavy chain can also be situated C-terminal to the polypeptide sequence derived from immunoglobulin light chain. The latter order is referred to as LC-HC. Non-limiting examples of fusion proteins consisting of a FVIII part joined to polypeptides assumed to protract FVIII by interaction with platelets are shown in Table 5.

Some fusion partners are presumed to delay in vivo clearance of FVIII by interaction with serum albumin. Non-limiting examples of fusion partners that assumingly protracts FVIII by interaction with serum albumin are single-chain anti-serum albumin antibodies (SC antiHSA) and albumin-binding polypeptides such as the ABD035 polypeptide. The albumin-binding polypeptides can be repeated several times, for instance 4 repetitions as present in 4XABD035 fusion partner. Non-limiting examples of fusion proteins consisting of a FVIII part joined to polypeptides assumed to protract FVIII by interaction with serum albumin are shown in Table 6.

Other fusion partners are presumed to delay in vivo clearance of FVIII by shielding. A non-limiting example of fusion partners that assumingly protracts FVIII by shielding is polypeptides with stretches of non-hydrophobic amino acids such as Sequence A (seq A) or repletion of elastin-like polypeptide (ELP) for instance ELP60. Non-limiting examples of fusion proteins consisting of a FVIII part joined to polypeptides assumed to protract FVIII by shielding are shown in Table 7.

Some fusion partners are presumed to delay in vivo clearance of FVIII by modulating the affinity to vWF. A non-limiting example of fusion partners that assumingly protracts FVIII by modulating the affinity to vWF is the a3 region of FVIII (amino acid 1649-1689 of wild-type human FVIII) or parts of the a3 region, thus adding one or more extra a3 regions to FVIII. Non-limiting examples of fusion proteins consisting of a FVIII part joined to polypeptides assumed to protract FVIII by modulating the affinity to vWF are shown in Table 8.

Some fusion partners are presumed to delay in vivo clearance of FVIII by mechanisms remaining to be determined. Non-limiting examples of fusion partners that assumingly protracts FVIII by mechanisms remaining to be determined are growth hormone binding protein (GHBP), parts of coagulation factor IX (FIX), parts of vWF, vWF binding protein, parts of chorion gonadotropin, and parts of coagulation factor X (FX). Non limiting examples of fusion partners derived from FIX are amino acid 298-342 of human FIX (FIX298-342) and amino acid 47-125 of human FIX (FIX47-125). Non-limiting examples of fusion partners derived from vWF are amino acid 1-272 of human vWF (vWF1-272), amino acid 1-1390 of human vWF (vWF1-1390, and amino acid 497-716 of human vWF (vWF497-716). A non-limiting example of fusion partners derived from chorion gonadotropin is the C-terminal 28 amino acids of the beta-chain of human chorion gonadotropin (hCG C-terminus). A non-limiting example of fusion partners derived from FX is the activation peptide of human FX (F10AP). Non-limiting examples of fusion proteins consisting of a FVIII part joined to polypeptides assumed to protract FVIII by mechanisms remaining to be determined are shown in Table 9.

Some fusion partners are presumed to delay in vivo clearance of FVIII by modulating the affinity to lipids. A non-limiting example of fusion partners that assumingly protracts FVIII by modulating the affinity to lipids is the C2 domain of FVIII, thus adding one or more extra C2 domains to FVIII. Non-limiting examples of fusion proteins consisting of a FVIII part joined to polypeptides assumed to protract FVIII by modulating the affinity to lipids are shown in Table 10

Fc receptor: Fc receptors are cell surface receptors that recognize and bind the Fc portion of antibodies. Based on structure, cell distribution and affinity to IgG, the Fc receptors are divided into three classes: FcγRI (CD64), FcγRII (CD32), and FCγRIII (CD16). According to the present invention, the Fc receptors fused to Factor VIII molecules may be of full length or partial length, as well as any variants thereof (variants include amino acid substitutions, deletions and additions). If they are of partial length it follows that the ability to bind antibodies should be retained.

Von Willebrandt Factor (vWF): vWF is a large mono-/multimeric glycoprotein present in blood plasma and produced constitutively in endothelium (in the Weibel-Palade bodies), megakaryocytes (α-granules of platelets), and subendothelial connective tissue. Its primary function is binding to other proteins, particularly Factor VIII and it is important in platelet adhesion to wound sites.

Factor VIII is bound to vWF while inactive in circulation; Factor VIII degrades rapidly or is cleared when not bound to vWF. It thus follows that reduction or abolishment of vWF binding capacity in FVIII has thus far been considered as a highly undesirable approach in obtaining Factor FVIII variants with prolonged circulatory half life.

The term "reduced capacity to bind vWF" is herein meant to encompass Factor VIII variants, wherein the capacity to bind vWF is decreased by at least 50%, preferably by at least 60%, more preferably by at least 70%, more preferably by at least 80%, more preferably by at least 90%, and most preferably about 100%. FVIII binding to vWF may be measured either by an ELISA like assay or as direct binding to immobilized vWF using surface plasmon resonance. The region in Factor VIII responsible for binding to vWF is the region spanning residues 1670-1684 as disclosed in EP0319315. It is envisaged that Factor VIII point and/or deltion mutatants involving this area will modify the ability to bind to vWF. Examples of particularly preferred point mutations according to the present invention include variants comprising one or more of the following point mutations: Y1680F, Y1680R, Y1680N, and E1682T, and Y1680C.

Factor VIII molecules: FVIII/Factor VIII is a large, complex glycoprotein that primarily is produced by hepatocytes. FVIII consists of 2351 amino acids, including signal peptide, and contains several distinct domains, as defined by homology. There are three A-domains, a unique B-domain, and two C-domains. The domain order can be listed as NH2-A1-A2-B-A3-C1-C2-COOH. FVIII circulates in plasma as two chains, separated at the B-A3 border. The chains are connected by bivalent metal ion-bindings. The A1-A2-B chain is termed the heavy chain (HC) while the A3-C1-C2 is termed the light chain (LC).

Endogenous Factor VIII molecules circulate in vivo as a pool of molecules with B domains of various sizes. What probably occurs in vivo is a gradual enzymatic removal of the B domain resulting in a pool of molecules with B-domains of various sizes. It is generally believed that cleavage at position 740, by which the last part of the B-domain is removed, occurs in connection with thrombin activation. However, it cannot be ruled out that a Factor VIII variant in which e.g. the cleavage site at position 740 has been impaired may be active.

"Factor VIII" or "FVIII" as used herein refers to a human plasma glycoprotein that is a member of the intrinsic coagulation pathway and is essential to blood coagulation. "Native FVIII" is the full length human FVIII molecule as shown in SEQ ID NO. 1 (amino acid 1-2332). The B-domain is spanning amino acids 741-1648 in SEQ ID NO 1.

SEQ ID NO 1:
ATRRYYLGAVELSWDYMQSDLGELPVDARFPPRVPKSFPFNTSVVYKKTLFVEFT

DHLFNIAKPRPPWMGLLGPTIQAEVYDTVVITLKNMASHPVSLHAVGVSYWKASEGAEYDD

QTSQREKEDDKVFPGGSHTYVWQVLKENGPMASDPLCLTYSYLSHVDLVKDLNSGLIGALL

VCREGSLAKEKTQTLHKFILLFAVFDEGKSWHSETKNSLMQDRDAASARAWPKMHTVNGY

VNRSLPGLIGCHRKSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDLTDSEMDVVRF

DDDNSPSFIQIRSVAKKHPKTWVHYIAAEEEDWDYAPLVLAPDDRSYKSQYLNNGPQRIGR

KYKKVRFMAYTDETFKTREAIQHESGILGPLLYGEVGDTLLIIFKNQASRPYNIYPHGITDVRP

LYSRRLPKGVKHLKDFPILPGEIFKYKWTVTVEDGPTKSDPRCLTRYYSSFVNMERDLASGLI

GPLLICYKESVDQRGNQIMSDKRNVILFSVFDENRSWYLTENIQRFLPNPAGVQLEDPEFQA

SNIMHSINGYVFDSLQLSVCLHEVAYVVYILSIGAQTDFLSVFFSGYTFKHKMVYEDTLTLFPF

SGETVFMSMENPGLWILGCHNSDFRNRGMTALLKVSSCDKNTGDYYEDSYEDISAYLLSKN

NAIEPRSFSQNSRHPSTRQKQFNATTIPENDIEKTDPWFAHRTPMPKIQNVSSSDLLMLLRQ

SPTPHGLSLSDLQEAKYETFSDDPSPGAIDSNNSLSEMTHFRPQLHHSGDMVFTPESGLQL

RLNEKLGTTAATELKKLDFKVSSTSNNLISTIPSDNLAAGTDNTSSLGPPSMPVHYDSQLDTT

LFGKKSSPLTESGGPLSLSEENNDSKLLESGLMNSQESSWGKNVSSTESGRLFKGKRAHG

PALLTKDNALFKVSISLLKTNKTSNNSATNRKTHIDGPSLLIENSPSVWQNILESDTEFKKVTP

LIHDRMLMDKNATALRLNHMSNKTTSSKNMEMVQQKKEGPIPPDAQNPDMSFFKMLFLPES

ARWIQRTHGKNSLNSGQGPSPKQLVSLGPEKSVEGQNFLSEKNKVVVGKGEFTKDVGLKE

MVFPSSRNLFLTNLDNLHENNTHNQEKKIQEEIEKKETLIQENVVLPQIHTVTGTKNFMKNLF

LLSTRQNVEGSYDGAYAPVLQDFRSLNDSTNRTKKHTAHFSKKGEEENLEGLGNQTKQIVE

KYACTTRISPNTSQQNFVTQRSKRALKQFRLPLEETELEKRIIVDDTSTQWSKNMKHLTPSTL

TQIDYNEKEKGAITQSPLSDCLTRSHSIPQANRSPLPIAKVSSFPSIRPIYLTRVLFQDNSSHL

PAASYRKKDSGVQESSHFLQGAKKNNLSLAILTLEMTGDQREVGSLGTSATNSVTYKKVEN

TVLPKPDLPKTSGKVELLPKVHIYQKDLFPTETSNGSPGHLDLVEGSLLQGTEGAIKWNEAN

RPGKVPFLRVATESSAKTPSKLLDPLAWDNHYGTQIPKEEWKSQEKSPEKTAFKKKDTILSL

NACESNHAIAAINEGQNKPEIEVTWAKQGRTERLCSQNPPVLKRHQREITRTTLQSDQEEID

YDDTISVEMKKEDFDIYDEDENQSPRSFQKKTRHYFIAAVERLWDYGMSSSPHVLRNRAQS

GSVPQFKKVVFQEFTDGSFTQPLYRGELNEHLGLLGPYIRAEVEDNIMVTFRNQASRPYSFY

-continued

```
SSLISYEEDQRQGAEPRKNFVKPNETKTYFWKVQHHMAPTKDEFDCKAWAYFSDVDLEKD

VHSGLIGPLLVCHTNTLNPAHGRQVTVQEFALFFTIFDETKSWYFTENMERNCRAPCNIQME

DPTFKENYRFHAINGYIMDTLPGLVMAQDQRIRWYLLSMGSNENIHSIHFSGHVFTVRKKEE

YKMALYNLYPGVFETVEMLPSKAGIWRVECLIGEHLHAGMSTLFLVYSNKCQTPLGMASGHI

RDFQITASGQYGQWAPKLARLHYSGSINAWSTKEPFSWIKVDLLAPMIIHGIKTQGARQKFS

SLYISQFIIMYSLDGKKWQTYRGNSTGTLMVFFGNVDSSGIKHNIFNPPIIARYIRLHPTHYSIR

STLRMELMGCDLNSCSMPLGMESKAISDAQITASSYFTNMFATWSPSKARLHLQGRSNAW

RPQVNNPKEWLQVDFQKTMKVTGVTTQGVKSLLTSMYVKEFLISSSQDGHQWTLFFQNGK

VKVFQGNQDSFTPVVNSLDPPLLTRYLRIHPQSWVHQIALRMEVLGCEAQDLY
```

The factor VIII molecules according to the present invention may be B domain truncated Factor FVIII molecules wherein the remaining domains correspond closely to the sequence as set forth in amino acid no 1-740 and 1649-2332 in SEQ ID NO 1 although there may also e.g. be one or more alterations within the vWF binding region between residues 1670-1684. However, B domain truncated molecules according to the invention may differ slight from the sequence set forth in SEQ ID NO 1, meaning that the remaining domains (i.e. the three A-domains and the two C-domains) may differ slightly e.g. 1, 2, 3, 4, 5, 6, 7, 8, 9, or amino acids or about 1%, 2%, 3%, 4% or 5% from the amino acid sequence as set forth in SEQ ID NO 1 (amino acids 1-740 and 1649-2332) due to the fact that mutations can be introduced in order to reduce e.g. vWF binding capacity. Furthermore, it is plausible that amino acid modifications (substitutions, deletions, etc.) are introduced other places in the molecule in order to modify the binding capacity of Factor VIII with various other components such as e.g. LRP, various receptors, other coagulation factors, cell surfaces, introduction and/or abolishment of glycosylation sites, etc.

Factor VIII molecules according to the present invention have Factor VIII activity, meaning the ability to function in the coagulation cascade in a manner functionally similar or equivalent to FVIII, induce the formation of FXa via interaction with FIXa on an activated platelet, and support the formation of a blood clot. The activity can be assessed in vitro by techniques well known in the art such as e.g. clot analysis, endogenous thrombin potential analysis, etc. Factor VIII molecules according to the present invention have FVIII activity being at least about 10%, at least 20%, at least 30%, at least 40%, at least 50%, at least 60%, at least 70%, at least 80%, at least 90%, and 100% or even more than 100% of that of native human FVIII.

B domain: The B-domain in Factor VIII spans amino acids 741-1648 in SEQ ID NO 1. The B-domain is cleaved at several different sites, generating large heterogeneity in circulating plasma FVIII molecules. The exact function of the heavily glycosylated B-domain is unknown. What is known is that the domain is dispensable for FVIII activity in the coagulation cascade. This apparent lack of function is supported by the fact that B domain deleted/truncated FVIII appears to have in vivo properties identical to those seen for full length native FVIII. That being said there are indications that the B-domain may reduce the association with the cell membrane, at least under serum free conditions.

B domain truncated/deleted Factor VIII molecule: Endogenous full length FVIII is synthesized as a single-chain precursor molecule. Prior to secretion, the precursor is cleaved into the heavy chain and the light chain. Recombinant B domain-deleted FVIII can be produced from two different strategies. Either the heavy chain without the B-domain and the light chain are synthesized individually as two different polypeptide chains (two-chain strategy) or the B-domain deleted FVIII is synthesized as a single precursor polypeptide chain (single-chain strategy) that is cleaved into the heavy and light chains in the same way as the full-length FVIII precursor.

In a B domain-deleted FVIII precursor polypeptide, the heavy and light chain moieties are normally separated by a linker. To minimize the risk of introducing immunogenic epitopes in the B domain-deleted FVIII, the sequence of the linker is preferable derived from the FVIII B-domain. As a minimum, the linker must comprise a recognition site for the protease that separates the B domain-deleted FVIII precursor polypeptide into the heavy and light chain. In the B domain of full length FVIII, amino acid 1644-1648 constitutes this recognition site. The thrombin site leading to removal of the linker on activation of B domain-deleted FVIII is located in the heavy chain. Thus, the size and amino acid sequence of the linker is unlikely to influence its removal from the remaining FVIII molecule by thrombin activation. Deletion of the B domain is an advantage for production of FVIII. Nevertheless, parts of the B domain can be included in the linker without reducing the productivity. The negative effect of the B domain on productivity has not been attributed to any specific size or sequence of the B domain.

The truncated B-domain may contain several O-glycosylation sites. However, according to a preferred embodiment, the molecule comprises only one, alternatively two, three or four O-linked oligosaccharides in the truncated B-domain.

According to a preferred embodiment, the truncated B domain comprises only one potential O-glycosylation sites and a side chain, such as e.g. PEG or an albumin binder is covalently conjugated to this O-glycosylation site.

The O-linked oligosaccharides in the B-domain truncated molecules according to the invention may be attached to O-glycosylation sites that were either artificially created by recombinant means and/or by exposure of "hidden" O-glycosylation sites by truncation of the B-domain. In both cases, such molecules may be made by designing a B-domain trunctated Factor VIII amino acid sequence and subsequently subjecting the amino acid sequence to an in silico analysis predicting the probability of O-glycosylation sites in the truncated B-domain. Molecules with a relatively high probability of having such glycosylation sites can be synthesized in a suitable host cell followed by analysis of the glycosylation pattern and subsequent selection of molecules having O-linked glycosylation in the truncated B-domain.

The Factor VIII molecule also contains a number of N-linked oligosaccharides and each of these may likewise serve as an anchor for attachment of a hydrophobic side group.

Suitable host cells for producing recombinant factor VIII fusion proteins according to the invention are preferably of mammalian origin in order to ensure that the molecule is glycosylated. In practicing the present invention, the cells are mammalian cells, more preferably an established mammalian cell line, including, without limitation, CHO, COS-1, baby hamster kidney (BHK), and HEK293 cell lines. Other suitable cell lines include, without limitation, Rat Hep I, Rat Hep II, TCMK, Human lung, DUKX cells (CHO cell line) Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. DUKX cells (CHO cell line) are especially preferred.

Currently preferred cells are HEK293, COS, Chinese Hamster Ovary (CHO) cells, Baby Hamster Kidney (BHK) and myeloma cells, in particular Chinese Hamster Ovary (CHO) cells.

The length of the B domain in the wt FVIII molecule is about 908 amino acids. The length of the truncated B domain in molecules according to the present invention may vary from about 10 to about 800 amino acids, such as e.g. from about 10 amino acids to about 700 acids, such as e.g. about 12-500 amino acids, 12-400 amino acids, 12-300 amino acids, 12-200 amino acids, 15-100 amino acids, 15-75 amino acids, 15-50 amino acids, 15-45 amino acids, 20-45 amino acids, 20-40 amino acids, or 20-30 amino acids. The truncated B-domain may comprise fragments of the heavy chain and/or the light chain and/or an artificially introduced sequence that is not found in the wt FVIII molecule. The terms "B-domain truncated" and "B-domain deleted" may be used interchangeably herein.

Modified circulatory half life: Molecules according to the present invention have a modified circulatory half life compared to the wild type Factor VIII molecule, preferably an increased circulatory half life. Circulatory half life is preferably increased at least 10%, preferably at least 15%, preferably at least 20%, preferably at least 25%, preferably at least 30%, preferably at least 35%, preferably at least 40%, preferably at least 45%, preferably at least 50%, preferably at least 55%, preferably at least 60%, preferably at least 65%, preferably at least 70%, preferably at least 75%, preferably at least 80%, preferably at least 85%, preferably at least 90%, preferably at least 95%, preferably at least 100%, more preferably at least 125%, more preferably at least 150%, more preferably at least 175%, more preferably at least 200%, and most preferably at least 250% or 300%. Even more preferably, such molecules have a circulatory half life that is increased at least 400%, 500%, 600%, or even 700%.

Hydrophilic polymer: The side group according to the present invention is preferably a non-naturally occurring hydrophilic polymer comprising at least one non-naturally occurring polymeric moiety. In another example, the non-naturally occurring modifying group is a modified carbohydrate.

Exemplary hydrophilic polymers according to the invention include water soluble polymers that can be linear or branched and can include one or more independently selected polymeric moieties, such as poly(alkylene glycol) and derivatives thereof. The polymeric modifying group according to the invention may include a water-soluble polymer, e.g. poly(ethylene glycol) and derivatived thereof (PEG, m-PEG), poly(propylene glycol) and derivatives thereof (PPG, m-PPG) and the like.

The polymer backbone of the water-soluble polymer according to the invention can be poly(ethylene glycol) (i.e. PEG). The term PEG in connection with the present invention includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine or cysteine. In one example, the branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly ([alpha]-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, as well as copolymers, terpolymers, and mixtures thereof.

Although the molecular weight of each chain of the polymer backbone can vary, it is typically in the range of from about 100 Da to about 160,000 Da, such as e.g. from about 5,000 Da to about 100,000 Da. More specifically, the size of each conjugated hydrophilic polymer according to the present invention may vary from about 500 Da to about 80,000 Da, such as e.g. about 1000 Da to about 80,000 Da; about 2000 Da to about 70,000 Da; about 5000 to about 70,000 Da; about 5000 to about 60,000 Da; about 10,000 to about 70,000 Da; about 20,000 to about 60,000 Da; about 30,000 to about 60,000 Da; about 30,000 to about 50,000 Da; or about 30,000 to about 40,000 Da. It should be understood that these sizes represent estimates rather than exact measures. According to a preferred embodiment, the molecules according to the invention are conjugated with a heterogenous population of hydrophilic polymers, such as e.g. PEG of a size of e.g. 10,000, 40,000, or 80,000 Da+/− about 5000, about 4000, about 3000, about 2000, or about 1000 Da.

Side chain/side group: The Factor VIII molecules according to the present invention may also be conjugated with side groups other than hydrophilic polymers. The side chain according to the present invention may e.g. be selected from one or more of the list consisting of: fatty acids and derivates thereof (sometimes referred to as "albumin binders"), peptides, etc., The hydrophobic side groups according to the invention are preferably biologically degradable. There may furthermore be more than one hydrophobic side group conjugated to an individual Factor VIII molecule, e.g. 2, 3, 4, 5, 6, 7, 8, 9, 10 or more. It furthermore follows that it is possible to conjugate Factor VIII molecules according to the invention with one or more hydrophobic side groups as well as one or more hydrophobic side groups, peptidic side groups, etc.

An individual Factor VIII molecule according to the invention may thus comprise side groups of e.g. both hydrophilic and hydrophobic/peptidic nature. It is nevertheless associated with additional efforts to conjugate the molecule with different types of side groups and such solutions may thus turn out to be relatively impractical in practice. The molecules according to the present invention thus preferably comprise only one type of side chains (e.g. hydrophilic/hydrophobic side chains).

Conjugation of Factor VIII with hydrophobic side groups has thus far, however, not been considered being an attractive alternative to conjugation with hydrophilic groups. One explanation may be that laborious and/or harsh chemical methods employing organic solvents would have been expected to be required. Another explanation may be that the usually relatively small hydrophobic molecules cannot be expected to be efficient in binding a conjugated (large) Factor VIII molecule to e.g. albumin and thereby possibly shielding the molecule from clearance.

Albumin Binder Conjugates

It is known that the in vivo properties of such proteins can be improved by the use of albumin binding side chains. Such side chains, or albumin binders, can be attached to the protein prior to administration and can, for example, stabilise the protein in vivo or improve or extend the in vivo half-life of the protein.

The albumin binder may thereby promote the circulation of the derivative with the blood stream. The albumin binder may have the effect of extending or protracting the time of action of the protein that it is bound to it, due to the fact that the complexes of the peptide derivative and albumin are only slowly disintegrated to release the active pharmaceutical ingredient. Thus, a preferred substituent, or side chain, as a whole may be referred to as an albumin binding moiety.

The albumin binder (albumin binding moiety) may comprise a portion which is particularly relevant for the albumin binding and thereby the protraction of circulation in the blood stream, which portion may accordingly be referred to as a protracting moiety. The protracting moiety is preferably at, or near, the opposite end of the albumin binding moiety as compared to its point of attachment to the peptide.

In a preferred embodiment, the albumin binder is, or comprises, a side chain that is capable of forming non-covalent complexes with albumin. The albumin binder may bind albumin non-covalently and/or reversibly. The albumin binder may bind albumin specifically. As is clear from the methods described below, the albumin binder may bind to cyclodextrin. The albumin binder may bind cyclodextrin non-covalently and/or reversibly. The albumin binder may bind cyclodextrin specifically.

An albumin binder as described herein is generally a hydrophobic group.

The other portion of the albumin binding moiety, i.e. the portion in-between the protracting moiety and the point of attachment to the peptide, may be referred to as a linker moiety, linker, spacer, or the like. However, the presence of such a linker is optional, and hence the albumin binding moiety may be identical to the protracting moiety.

In particular embodiments, the albumin binding moiety and/or the protracting moiety is lipophilic, and/or negatively charged at physiological pH (7.4).

The albumin binding moiety and/or the protracting moiety may be covalently attached to an amino group of the peptide by conjugation chemistry such as by alkylation, acylation, or amide formation; or to a hydroxyl group, such as by esterification, alkylation, oximation.

In a preferred embodiment, an active ester of the albumin binding moiety and/or the protracting moiety is covalently linked to an amino group of a sialic acid residue or a sialic acid derivative, under formation of an amide bond (this process being referred to as acylation).

Unless otherwise stated, when reference is made to an acylation of a protein, it is understood to be to an amino-group linked to a sialic acid residue on on glycoprotein.

For the present purposes, the terms "albumin binding moiety", "protracting moiety", and "linker" include the un-reacted as well as the reacted forms of these molecules. Whether or not one or the other form is meant is clear from the context in which the term is used.

The albumin binding moiety may be, or may comprise a fatty acid or fatty diacid or a derivative or either thereof.

The term "fatty acid" refers to aliphatic monocarboxylic acids having from 4 to 28 carbon atoms, such as 16 carbon atoms. It is preferably unbranched, and/or even numbered, and it may be saturated or unsaturated.

The term "fatty diacid" refers to fatty acids as defined above but with an additional carboxylic acid group in the omega position. Thus, fatty diacids are dicarboxylic acids.

The nomenclature is as is usual in the art, for example —COOH, as well as HOOC—, refers to carboxy; —$C_6H_4$— to phenylen; —CO—, as well as —OC—, to carbonyl (O=C<); and $C_6H_5$—O— to phenoxy.

In a preferred embodiment the linker moiety, if present, has from 2 to 80 C-atoms, preferably from 5 to 70 C-atoms. In additional preferred embodiments, the linker moiety, if present, has from 4 to 20 hetero atoms, preferably from 2 to 40 hetero atoms, more preferably from 3 to 30 hetero atoms. Particularly preferred examples of hetero atoms are N-, and O-atoms. H-atoms are not hetero atoms.

In another embodiment, the linker comprises at least one OEG molecule, and/or at least one glutamic acid residue, or rather the corresponding radicals (OEG designates 8-amino-3,6-dioxaoctanic acid, i.e. this radical: —NH—$(CH_2)_2$—O—$(CH_2)_2$—O—$CH_2$—CO—).

In one preferred embodiment, the linker moiety comprises a di-carboxyl residue linked to a sialic acid residue by an amide bond. In preferred examples, the di-carboxyl residue has from 2-30 C-atoms, preferably 4-20 C-atoms, more preferably 4-10 C-atoms. In additional preferred examples, the di-carboxyl residue has from 0-10 hetero-atoms, preferably 0-5 hetero-atoms.

In another preferred example, the linker moiety comprises a group containing both an amino and a distal carboxyl-group linked to a sialic acid residue by an amide bond through its distal carboxyl groups. In one preferred embodiment the this group is an OEG group.

The amino acid glutamic acid (Glu) comprises two carboxylic acid groups. Its gamma-carboxy group is preferably used for forming an amide bond with an amino group of a sialic acid residue or a sialic acid derivative, or with an amino group of an OEG molecule, if present, or with the amino group of another Glu residue, if present. The amino group of Glu in turn forms an amide bond with the carboxy group of the protracting moiety, or with the carboxy group of an OEG molecule, if present, or with the gamma-carboxy group of another Glu, if present. This way of inclusion of Glu is occasionally briefly referred to as "gamma-Glu".

Without being bound by theory it is envisaged that the reason why it may be advantageous to attach hydrophobic side groups to Factor VIII molecules with reduced vWF binding capacity rather than attaching such side groups to Factor VIII molecules with normal vWF binding capacity is that the relative size of the side group is relatively small in the large Factor VIII/vWF complex. It is hypothesized that a relatively large side group functions more efficiently in shielding the free Factor VIII from clearance. It is further hypothesized that the half life of FVIII is related to that of vWF. FVIII molecules with reduced ability to bind vWF most likely have exposed clerance epitopes which would normally have been shielded by vWF. By attaching side groups it is thus hypothesized that this "clearance shielding" can be regained. In other cases, attachment of side groups such as e.g. antibody fragments may function by e.g. attaching the molecule to proteins, cells, or platelets having a relatively long circulatory half life.

O-linked oligosaccharide: Both N-glycans and O-glycans are attached to proteins by the cells producing the protein. The cellular N-glycosylation machinery recognizes and glycosylates N-glycosylation signals (N—X—S/T motifs) in the amino acid chain, as the nascent protein is translocated from the ribosome to the endoplasmic reticulum (Kiely et al. 1976; Glabe et al. 1980).

Likewise, O-glycans are attached to specific O-glycosylation sites in the amino acid chain, but the motifs triggering O-glycosylation are much more heterogenous than the N-glycosylation signals, and our ability to predict O-glycosylation sites in amino acid sequences is still inadequate (Julenius et al. 2004). The construction of artificial O-glycosylation sites it is thus associated with some uncertainty.

Linkage of hydrophobic side groups: Conjugation of Factor FVIII molecules with hydrophobic side groups may be made using chemical methods. However, a number of advantages are potentially associated with employment of an enzymatic approach. According to a preferred enzymatic method according to the present invention, [hydrophobic protractor group]-sialyl-CMP substrate can be prepared chemically. This substrate can be transferred enzymatically to glycans present on Factor FVIII using a sialyltransferase enzyme. The inventors of the present invention have surprisingly demonstrated that this enzymatic approach can be performed without addition of any organic solvents that may. A number of disadvantages are associated with use of organic solvents, e.g. loss of biological activity, environmental concerns, additional steps to be taken to ensure that the organic solvents are completely removed, etc. It may also be possible to avoid addition of cyclodextrin-cyclodextrin is a detergent which may also contribute to loss of biological function. In the process of enzymatic conjugation, it may be an advantage to add glycerol, e.g. 5-30% glycerol, preferably 10-20% glycerol. The presence of glycerol seem to stabilize the Factor VIII molecule e.g. in the freeze/thaw process and it may also prevent formation of Factor VIII crystals. Glycerol present during enzymatic conjugation does thus not need to be removed after the conjugation process has been completed.

Sialyltransferase: Sialyltransferases are enzymes that transfer sialic acid to nascent oligosaccharide. Each sialyltransferase is specific for a particular sugar substrate. Sialyltransferases add sialic acid to the terminal portions of the sialylated glycolipids (gangliosides) or to the N- or O-linked sugar chains of glycoproteins. There are about twenty different sialyltransferases which can be distinguished on the basis of the acceptor structure on which they act and on the type of sugar linkage they form. Preferred sialyltransferases according to the present invention are ST3Gal-I (specific for O-glycans) and ST3Gal-III (specific for N-glycans). It is thus possible to engineer the structure of the conjugated Factor VIII molecules according to the present invention by e.g. selection of a specific sialyltransferase and/or engineering of a Factor VIII molecule with a particular glycosylation pattern.

Pharmaceutical composition: A pharmaceutical composition is herein preferably meant to encompass compositions comprising Factor VIII molecules according to the present invention suitable for parenteral administration, such as e.g. ready-to-use sterile aqueous compositions or dry sterile compositions that can be reconstituted in e.g. water or an aqueous buffer. The compositions according to the invention may comprise various pharmaceutically acceptable excipients, stabilizers, etc.

Additional ingredients in such compositions may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the FVIII compound in the form of a nasal or pulmonal spray. As a still further option, the pharmaceutical compositions containing the FVIII compound of the invention may also be adapted to transdermal administration, e.g. by needlefree injection or from a patch, optionally an iontophoretic patch, or transmucosal, e.g. buccal, administration.

The term "treatment", as used herein, refers to the medical therapy of any human or other animal subject in need thereof. Said subject is expected to have undergone physical examination by a medical practitioner, who has given a tentative or definitive diagnosis which would indicate that the use of said specific treatment is beneficial to the health of said human or other animal subject. The timing and purpose of said treatment may vary from one individual to another, according to the status quo of the subject's health. Thus, said treatment may be prophylactic, palliative, symptomatic and/or curative.

In a first aspect, the present invention relates to a recombinant Factor VIII molecule, wherein said Factor VIII molecule is a fusion protein comprising a Factor VIII molecule and a fusion partner. In a first embodiment, the fusion partner is replacing the a3-domain of the Factor VIII molecule. The small a3-domain of Factor VIII may thus be fully or partly replaced by the fusion partner. In a second embodiment, the fusion partner is inserted into the B-domain of Factor VIII. The B-domain may be a full length B-domain but in a preferred embodiment, the B domain is significantly truncated. There will thus be at least three, four, five, six, seven, eight, nine or ten amino acids originating from the B-domain at both the N- and the C-terminal ends of the fusion partner. In another preferred embodiment, the fusion partner is inserted in or at the C-terminal end of the C2 domain in Factor FVIII.

In a third embodiment, the Factor VIII molecule according to the invention is fused to an antibody binding molecule such as e.g. an Fc receptor. Examples of antibody binding molecules are listed in the tables below. In a fourth embodiment, the Factor VIII molecule is fused to a molecule having the capability of binding to human serum albumin. In another embodiment, the Factor VIII is fused to transferrin. Examples thereof are also provided below. In a fifth embodiment, the Factor VIII molecule is fused with a molecule having the capability of binding to platelets—specific examples of such molecules are likewise provided below. In yet another embodiment, the Factor VIII molecule is fused to a molecule with the capacity of binding to a Factor VIII clearance receptor.

In a sixth embodiment, the Factor VIII molecule according to the invention has reduced vWF binding capacity. Preferably, such Factor VIII molecules comprise a mutation (substitution, deletion or addition of amino acids) within the area spanning amino acids 1670-1684 in SEQ ID N01. Most preferably, such Factor VIII molecules comprise one of the following point mutations: Y1680F, Y1680R, Y1680N, and E1682T, and Y1680C.

In a seventh embodiment, the molecule according to the invention is conjugated with a side group. This side group may be selected from one or more of the list consisting of: hydrophilic polymers, peptides and hydrophobic side groups. Preferably, the side group is a PEG group, a fatty acid derivative, or a polypeptide. Preferably, such side groups are attached to the molecule using enzymatic approaches, such as e.g. the technology disclosed in WO0331464, wherein O-linked and/or N-linked glycans are used as linkers.

Another aspect of the present invention relates to FVIII molecule fused to a fusion partner, wherein the fusion partner is replacing the A3-domain of the Factor VIII molecule.

In one embodiment, the fusion partner is albumin. In another embodiment, the fusion partner is an Fc receptor. In another embodiment, the Fc receptor is FcγRI. In another embodiment, the fusion partner is an Fc domain. In another embodiment, the Fc domain is a mutated Fc domain having reduced effector functions and/or increased affinity to the neonatal Fc receptor. In another embodiment, the fusion protein is conjugated with a side group. In another embodiment, the side group is linked to the fusion protein via an N-linked and/or an O-linked glycan. In another embodiment, the side group is linked to an N-linked and/or an O-linked glycan via a sialic acid. In another embodiment, the side group is selected from one or more of the list consisting of hydrophilic polymers, peptides, and hydrophobic side groups. In another embodiment, the FVIII molecule is a B domain truncated molecule wherein the B domain comprises the sequence as set forth in SEQ ID NO 2. In another embodiment, the fusion protein comprises a side group linked to the O-linked glycan in the truncated B domain that comprises the amino acid sequence as set forth in SEQ ID NO 2. In another embodiment, the Factor VIII molecule has reduced vWF binding capacity. In another embodiment, the Factor VIII molecule having reduced vWF binding capacity comprises a mutation selected from the list consisting of: Y1680F, Y1680R, Y1680N, and E1682T, and Y1680C.

Another aspect of the present invention relates to a FVIII molecule fused to a fusion partner, wherein the fusion partner is inserted into the B-domain of Factor VIII.

In one embodiment, the fusion partner is albumin. In another embodiment, the fusion partner is an Fc receptor. In another embodiment, the Fc receptor is FcγRI. In another embodiment, the fusion partner is an Fc domain. In another embodiment, the Fc domain is a mutated Fc domain having reduced effector functions and/or increased affinity to the neonatal Fc receptor. In another embodiment, the fusion protein is conjugated with a side group. In another embodiment, the side group is linked to the fusion protein via an N-linked and/or an O-linked glycan. In another embodiment, the side group is linked to an N-linked and/or an O-linked glycan via a sialic acid. In another embodiment, the side group is selected from one or more of the list consisting of hydrophilic polymers, peptides, and hydrophobic side groups. In another embodiment, the FVIII molecule is a B domain truncated molecule wherein the B domain comprises the sequence as set forth in SEQ ID NO 2. In another embodiment, the fusion protein comprises a side group linked to the O-linked glycan in the truncated B domain that comprises the amino acid sequence as set forth in SEQ ID NO 2. In another embodiment, the Factor VIII molecule has reduced vWF binding capacity. In another embodiment, the Factor VIII molecule having reduced vWF binding capacity comprises a mutation selected from the list consisting of: Y1680F, Y1680R, Y1680N, and E1682T, and Y1680C.

Another aspect of the present invention relates to a FVIII molecule fused to a fusion partner, wherein the fusion partner is inserted in the C-terminal end of the C2 domain in Factor FVIII.

In one embodiment, the fusion partner is albumin. In another embodiment, the fusion partner is an Fc receptor. In another embodiment, the Fc receptor is FcγRI. In another embodiment, the fusion partner is an Fc domain. In another embodiment, the Fc domain is a mutated Fc domain having reduced effector functions and/or increased affinity to the neonatal Fc receptor. In another embodiment, the fusion protein is conjugated with a side group. In another embodiment, the side group is linked to the fusion protein via an N-linked and/or an O-linked glycan. In another embodiment, the side group is linked to an N-linked and/or an O-linked glycan via a sialic acid. In another embodiment, the side group is selected from one or more of the list consisting of hydrophilic polymers, peptides, and hydrophobic side groups. In another embodiment, the FVIII molecule is a B domain truncated molecule wherein the B domain comprises the sequence as set forth in SEQ ID NO 2. In another embodiment, the fusion protein comprises a side group linked to the O-linked glycan in the truncated B domain that comprises the amino acid sequence as set forth in SEQ ID NO 2. In another embodiment, the Factor VIII molecule has reduced vWF binding capacity. In another embodiment, the Factor VIII molecule having reduced vWF binding capacity comprises a mutation selected from the list consisting of: Y1680F, Y1680R, Y1680N, and E1682T, and Y1680C.

Another aspect relates to a method of making a molecule according to the present invention, wherein said method comprises incubating a host cell encoding said molecule under appropriate conditions. Accordingly, the present invention also relates to nucleic acids molecules as well as expression vectors and host cells comprising nucleic acid seqences that encode a molecule according to the present invention. Molecules obtained by or obtainable by such methods are likewise an aspect of the present invention.

Another aspect relates to use of a molecule according to the present invention as a medicine.

Another aspect relates to use of a molecule according to the present invention for treatment of haemophilia, preferably haemophilia A.

Another aspect relates to a pharmaceutical composition comprising a molecule according to the invention and optionally one or more pharmaceutically acceptable excipients.

Another aspect of the invention relates to a method of treatment of a haemophilic disease comprising administering to a patient in need thereof a therapeutically effective amount of a molecule according to the present invention.

EXAMPLES

Example 1

FVIII Frameworks and Fusion Partners

The fusion proteins of the present invention consist of a FVIII protein (FVIII part) joined to a polypeptide (fusion partner) from another protein.

The FVIII part of the fusion protein can be any protein with FVIII activity. The FVIII part can be a B domain-deleted/truncated (BDD) FVIII protein, in which parts of the FVIII B domain has been removed from the protein. Non-limiting examples of FVIII frameworks that can constitute the FVIII part of fusion proteins is shown in Table 1. F8-500 is a BDD human FVIII protein. Starting at the N-terminus, F8-500 consists of FVIIIs signal peptide (amino acid −19 to −1) followed by FVIII HC without the B domain (amino acid 1-740), a 21 amino acid linker (SFSQNSRHPSQN-PPVLKRHQR) (SEQ ID NO 2), and FVIII LC (amino acid 1649-2332 of wild-type human FVIII. The sequence of the 21 amino acid linker is derived from the B domain of FVIII and consists of amino acid 741-750 and 1638-1648 of full-length wild-type human FVIII.

F8-500-Δa3 consists of F8-500 without the a3 region. In F8-500-Δa3 amino acid 1647-1687 of wild-type human FVIII is eliminated from F8-500. Thereby, the furin site at amino acid 1645-1648 is destroyed. A combined furin and thrombin site is, however, created by the R1645-H1646-P1688-R1689 amino acid stretch in F8-500-Δa. The a3 region is important for binding of FVIII to vWF and therefore, the affinity of F8-500-Δa3 for vWF is reduced compared to wild-type FVIII.

F8-500-His consists of F8-500 with a His tag inserted in the linker of F8-500. Thus the linker sequence of F8-500-His is SFSQNSRHPSHHHHHHSQNPPVLKRHQR (SEQ ID NO 3).

F8-500-Δa3-His consists of F8-500 without the a3 region but with a His tag inserted in the linker of F8-500. Thus, in F8-500-Δa3-His amino acid 1647-1687 of wild-type human FVIII has been eliminated from F8-500 and the linker sequence is SFSQNSRHPSHHHHHHSQNPPVLKRHQR (SEQ ID NO 4).

F8-500-Y1680F and F8-500-Y1680C consist of F8-500 in which amino acid 1680 of full-length wild-type human FVIII has been changed from tyrosine to phenylalanine and cysteine, respectively. Both these amino acid replacements reduce the affinity of FVIII to vWF factor. Furthermore, the Y1680C amino acid replacement introduces a free cysteine that can be used as a handle for conjugating protracting moieties to the fusion protein.

The fusion partner can be joined to several positions on the FVIII part of the fusion protein. Non-limiting examples of positions on FVIII for joining to the fusion partner are in the B domain or the B-domain-derived linker between the FVIII HC and LC, at the position of a3, and at the C-terminus of FVIII LC.

Example 2

Construction of Expression Vectors Encoding FVIII Frameworks and Fusion Proteins The fusions between FVIII and fusions partners all involves PCR for amplifying the fusion partner. Restriction sites are added to the ends of the PCR primers used. Restriction enzymes are used for cloning of fusion partner cDNA or synthetis DNA into FVIII cDNA.

Fusions in the B-domain of F8-500 takes place between aa750 and aa1638. Restriction sites AvrII, NruI, AgeI and MluI within or flanking the B-domain are used for insertion of the fusion partner encoding DNA.

For fusions at the carboxy terminus of FVIII light chain, the F8-500 coding construct is modified. The internal BamHI site (aa 604-606) is eliminated by site-directed mutagenesis and DNA encoding the flexible $(GGGS)_6$ linker is inserted 3' to the coding region. A new BamHI site is introduced in the 3' end of the linker-coding DNA in order to ease cloning of C-terminal fusion partners between BamHI and NotI sites. Subsequently, fusion partner DNA is inserted. The fusions proteins derived from this construct is referred to as F8-500-C2-linked-(GGGS)6-X in Table 2-12. Similar to the $(GGGS)_6$ linker a minimal GS-linker (BamHI restriction site) was inserted in the 3' end of the F8-500 coding region. The BamHI restriction site (GGATCC) form the two codons of GS (Glycine-Serine). The fusions proteins derived from this construct is referred to as F8-500-C2-linked-GS-X in Table 2-12. Fusions to the C-terminus of F8-500 without any linker were made by PCR amplifying the fusions with extended primers harboring the last 109 bp of the F8-500 coding region in the 5' end and a NotI restriction site in the 3' end of the PCR product. The XbaI restriction site is present 104-109 bp from the F8-500 stop codon. XbaI and NotI restriction enzymes were used for cloning the fusion partners without linkers. The fusions proteins derived from this latter construct is referred to as F8-500-C2-linked-X in Table 2-12.

For insertion of the fusion partner coding DNA at a3 positions thus replacing a3 with the fusion partner in the encoded protein, the SacII restriction site is introduced 3' to the coding region of a3. Thus, fusion partner coding DNA can be introduced by insertion between the AgeI and SacII sites or between the AvrII and SacII sites.

hFc
(SEQ ID NO 5)

htcppcpapeaegepsvflfppkpkdtlmisrtpevtcvvvdvshedpevkfnwyvdgvevhnaktkpreeqyqs tyrvvsvltvlhqdwlngkeykckvsnkalpapiektiskakgqprepqvytlppsrdeltknqvsltclykgfypsdiavewesng qpennykttppvldsdgsfflyskltvdksrwqqgnvfscsvmhealhnhytqkslslspgk -continued mFc (SEQ ID NO 6)
kpcppckcpapnaegepsyfifppkikdvlmislspmvtcvvvdvseddpdvqiswfvnnvevltaqtqthredyq
stlrvvsalpiqhqdwmsgkefkckvnnkalpapiertiskpkgsvrapqvyvlpppeeemtkkqvtltcmvtdfmpediyvewt
nngktelnyknt epvldsdgsyfmysklrvekknwvernsyscsvvheglhnhhttksfsrtpgk Human Serum Albumin (HSA) (SEQ ID NO 7)
Dahksevahrfkdlgeenfkalvliafaqylqqcpfedhvklvnevtefaktcvadesaencdkslhtlfgdklctvatlr
etygemadccakqepernecflqhkddnpnlprlvrpevdvmctafhdneetflkkylyeiarrhpyfyapellffakrykaaftec
cqaadkaacllpkldelrdegkassakqrlkcaslqkfgerafkawavarlsqrfpkaefaevsklvtdltkvhtecchgdllecadd
radlakyicenqdsissklkeccaaadphecyakvfdefkplveepqnlikqncelfeqlgeykfqnallvrytkkvpqvstptlvevsrnlgk
vgskccknpeakrmpcaedylsvvlnqlcvlhektpvsdrvtkccteslvnrrpcfsalevdetyvpkefnaetftfhadictlseker
qikkqtalvelvkhkpkatkeqlkaymddfaafvekccnaddketcfaeegkklvaasqaalgl Transferrin (SEQ ID NO 8)
VPDKTVRWCAVSEHEATKCQSFRDHMKSVIPSDGPSVACVKKASYLDCIRAIAANE
ADAVTLDAGLVYDAYLAPNNLKPVVAEFYGSKEDPQTFYAVAVVKKDSGFQMNQLRGKKS
CHTGLGRSAGWNIPIGLLYCDLPEPRKPLEKAVANFFSGSCAPCADGTDFPQLCQLCPGCG
CSTLNQYFGYSGAFKCLKDGAGDVAFVKHSTIFENLANKADRDQYELLCLDNTRKPVDEYK
DCHLAQVPSHTVVARSMG GKEDLIWELLNQAQEHFGKDKSKEFQLFSSPHG-
KDLLFKDSAHGFLKVPPRMDAKMYL
GYEYVTAIRNLREGTCPEAPTDECKPVKWCALSHHERLKCDEWSVNSVGKIECVSAETTED
CIAKIMNGEADAMSLDGGFVYIAGKCGLVPVLAENYNKSDNCEDTPEAGYFAVAVVKKSAS
DLTWDNLKGKKSCHTAVGRTAGWNIPMGLLYNKINHCRFDEFFSEGCAPGSKKDSSLCKLC
MGSGLNLCEPNNKEGYYGYTGAFRCLVEKGDVAFVKHQTVPQNTGGKNPDPWAKNLNEK
DYELLCLDGTRKPVEEYANCHLARAPNHAVVTRKDKEACVHKILRQQQHLFGSNVTDCSGN
FCLFRSETKDLLFRDDTVCLAKLHDRNTYEKYLGEEYVKAVGNLRKCSTSSLLEACTFRRP hFcγRI (CD64) (SEQ ID NO 9)
qvdttkavitlqppwvsvfgeetvtlhcevlhlpgssstqwflngtatqtstpsyritsasyndsgeyrcqrglsgrsdpiql
eihrgwlllqvssrvftegeplalrchawkdklvynvlyyrngkafkffhwnsnltilktnishngtyhcsgmgkhrytsagisvtvkelf
papvlnasvtspllegnlvtlscetklllqrpglqlyfsfyrngsktlrgrntsseyqiltarredsglywceaatedgnvlkrspelelqvlg
lqlptp FcRn (SEQ ID NO 10)
aeshlsllyhltayssspapgtpafwvsgwlgpqqylsynslrgeaepcgawywenqvswywekettdlrikeklfle
afkalggkgpytlqgllgcelgpdntsvptakfalngeefmnfdlkqgtwggdwpealaisqrwqqqdkaankeltfllfscphrlre
hlergrgnlewkeppsmrlkarpsspgfsvltcsafsfyppelqlrflrnglaagtgqgdfgpnsdgsfhassaltyksgdehhycci
vqhaglaqplrvelespakss FcRn-H166K (SEQ ID NO 11)
aeshlsllyhltavssspapgtpafwvsgwlgpqqylsynslrgeaepcgawywenqvswywekettdlrikeklfle
afkalggkgpytlqgllgcelgpdntsvptakfalngeefmnfdlkqgtwggdwpealaisqrwqqqdkaankeltfllfscphrlre
klergrgnlewkeppsmrlkarpsspgfsvltcsafsfyppelqlrflrnglaagtgqgdfgpnsdgsfhassaltyksgdehhycci
vqhaglaqplrvelespakss -continued LRP-CR5-6 (SEQ ID NO 12)
tcppnqfscasgrcipiswtcdldddcgdrsdesascayptcfpltqftcnngrcininwrcdndndcgdnsdeagc
sh LRP-CR6-7 (SEQ ID NO 13)
tcfpltqftcnngrcininwrcdndndcgdnsdeagcshscsstqfkcnsgrcipehwtcdgdndcgdysdethan
ctnqatr LRP-CR6 (SEQ ID NO 14)
tcfpltqftcnngrcininwrcdndndcgdnsdeagcsh SC anti-GPIIIa-1-HC-LC (SEQ ID NO 15)
mdilmtqspssmsyslgdtvsitchasqgissnigwlqqkpgksfmgliyygtnlvdgvpsrfsgsgsgadysltissl
dsedfadyycvqyaglpytfgggtklekelgggsggggsggggsnsvqlqqsgaelvkpgasvklsctasgfnikdtyvhwykq
rpeqglewigridpangytkydpkfqgkatitadtssntaylqlssltsedtavyycvrplydyyamdywgqgtsvtvss Linker-SC anti-GPIIIa-1-HC-LC (SEQ ID NO 16)
mdilmtqspssmsyslgdtvsitchasqgissnigwlqqkpgksfmgliyygtnlvdgypsrfsgsgsgadysltissl
dsedfadyycvqyaqlpytfgggtklekelgggsggggsggggsnsvqlqqsgaelvkpgasyklsctasgfnikdtyvhwykq
rpeqglewighdpangytkydpkfqgkatitadtssntaylqlssltsedtavyycyrplydyyamdywgqgtsvtvssggggsg
gggsggggs SC anti-GPIIIa-2-HC-LC (SEQ ID NO 17)
qvqlqqsgaelvrpgtsvkisckasgytftnywlgwykqrpghglewigdiypgggynkynenfkgkatltadtssst
aymqlssltsedsavyfcareygnydyamdswgqgtsvtvssggggsggggsggggsdivmtqaapsvpvtpgesysiscr
ssrsllhsngntylcwflqrpgqspqlliyrmsnlasgypdrfsgsgsgtaftlrisrveaedvgvyycniqhleypftfgsgtkleikr SC anti-GPIIIa-2-LC-HC (SEQ ID NO 18)
divmtqaapsvpvtpgesysiscrssrsllhsngntylcwflqrpgqspqlliyrmsnlasgypdrfsgsgsgtaftlrisr
veaedvgvyycmqhleypftfgsgtkleikrggggsggggsggggsqvqlqqsgaelvrpgtsvkisckasgytftnywlgwyk
qrpghglewigdiypgggynkynenfkgkatltadtssstaymqlssltsedsavyfcareygnydyamdswgqgtsvtvss ABD035 (SEQ ID NO 19)
laeakylanreldkygysdfykdinkaktvegyealklhilaalp Sequence A (SEQ ID NO 20)
GSPAGSPTSTEEGTSESATPESGPGTSTEPSEGSAPGSPAGSPTSTEEGTSTEPS
EGSAPGTSTEPSEGSAPGTSESATPESGPGSEPATSGSETPGSEPATSGSETPGSPAGSP
TSTEEGTSESATPESGPGTSTEPSEGSAPGTSTEPSEGSAPGSPAGSPTSTEEGTSTEPSE
GSAPGTSTEPSEGSAPGTSESATPESGPGTSTEPSEGSAPGTSESATPESGPGSEPATSG
SETPGTSTEPSEGSAPGTSTEPSEGSAPGTSESATPESGPGTSESATPESGPGSPAGSPTS
TEEGTSESATPESGPGSEPATSGSETPGTSESATPESGPGTSTEPSEGSAPGTSTEPSEGS
APGTSTEPSEGSAPGTSTEPSEGSAPGTSTEPSEGSAPGSPAGSPTSTE
EGTSTEPSEGSAPGTSESATPESGPGSEPATSGSETPGTSESATPESGPGSEPATSGSETP
GTSESATPESGPGTSTEPSEGSAPGTSESATPESGPGSPAGSPTSTEEGSPAGSPTSTEE
GSPAGSPTSTEEGTSESATPESGPGTSTEPSEGSAPGTSESATPESGPGSEPATSGSETP
GTSESATPESGPGSEPATSGSETPGTSESATPESGPGTSTEPSEGSAPGSPAGSPTSTEE
GTSESATPESGPGSEPATSGSETPGTSESATPESGPGSPAGSPTSTEEGSPAGSPTSTEE
GTSTEPSEGSAPGTSESATPESGPGTSESATPESGPGTSESATPESGPGSEPATSGSETP

GSEPATSGSETPGSPAGSPTSTEEGTSTEPSEGSAPGTSTEPSEGSAPGSEPATSGSETP

GTSESATPESGPGTSTEPSEGSAPG

ELP80 (SEQ ID NO 21)

gvpgvgvpgggvpgvgvpgvgvpgappgvgvpgggvpgvgvpgvgvpgappgvgvpgggvpgvgvpgv gvpgappgvgvpgggvpgvgvpgvgvpgappgvgvpgggvpgvgvpgvgvpgappgvgvpgggvpgv gvpgvgvpgappgvgvpgggvpgvgvpgvgvpgappgvgvpgggvpgvgvpgvgvpgappgvgvpgg gvpgvgvpgvgvpgappgvgvpgggvpgvgvpgvgvpgappgvgvpgggvpgvgvpgvgvpgappgv gvpggggvpgvgvpgvgvpgappgvgvpgggvpgvgvpgvgvpgappgvgvpgggvpgvgvpgvgvpga gvpgvgvpgggvpgvgvpgvgvpgagvpgvgvpgggvpgvgvpgvgvpga Extra a3 (SEQ ID NO 22)

eitrttlqsdgeeidyddtisvemkkedfdiydedengspr

GHBP (SEQ ID NO 23)

fsgseataailsrapwslgsvnpglktnsskepkftkcrsperetfschwtdevhhgtknlgpiqlfytrrntqewtqew kecpdyvsagenscyfnssftsiwipyciklтsnggtvdekcfsvdeivqpdppialnwtllnvsltgihadiqvrweaprnadiqkg wmyleyelqykevnetkwkmmdpilttsvpvyslkydkeyevrvrskqrnsgnygefsevlyvtlpqmsq

FIX298-342 (SEQ ID NO 24)

iflkfgsgyvsgwarvfhkgrsalvlqylryplvdratclrstkf

FIX47-125 (SEQ ID NO 25)

Ddgdqcesnpclnggsckddinsyecwcpfgfegknceldvtcnikngrceqfcknsadnkvvcsctegyrlaen qksce vWF1-272 (SEQ ID NO 26)

slscrppmvklvcpadnlraeglectktcqnydlecmsmgcvsgclcppgmvrhenrcvalercpcfhqgkeyap getvkigcntcvcrdrkwnctdhvcdatcstigmahyltfdglkylfpgecqyvlvgdycgsnpgtfrilvgnkgcshpsvkckkrvti lveggeielfdgevnykrpmkdethfevvesgryiiilllgkalsvvwdrhlsisvvlkqtyqekvcglcgnfdgiqnndltssnlqvee dpvdfgnswkvssqcadtr vWF1-1390 (SEQ ID NO 27)

slscrppmvklvcpadnlraeglectktcqnydlecmsmgcvsgcicppgmvrhenrcvalercpcfhqgkeyap getykigcntcvcrdrkwnctdhvcdatcstigmahyltfdglkylfpgecqyvlvgdycgsnpgtfrilvgnkgcshpsvkckkrvti lveggeielfdgevnvkrpmkdethfevvesgryiiilllgkalsvvwdrhlsisvvlkqtyqekvcglcgnfdgiqnndltssnlqvee dpvdfgnswkvssqcadtrkvpldsspatchnnimkqtmvdsscriltsdvfqdcnklvdpepyldvciydtcscesigdcacfc dtiaayahvcaqhgkvvtwrtatlcpqsceernlrengyecewrynscapacqvtcqhpeplacpvqcvegchahcppgkild ellqtcvdpedcpvcevagrrfasgkkvtlnpsdpehcqichcdvvnltceacqepgglvvpptdapyspttlyvediseppplhdf ycsrlldlvflldgssrlseaefevlkafvvdmmerlrisqkwvrvavveyhdgshayiglkdrkrpselrriasqvkyagsqvastse vlkytlfqifskidrpeasrialllmasqepqrmsrnfvryvqglkkkkvivipvgigphanlkgirliekqapenkafvlssvdeleqqr deivsylcdlapeappptlppdmaqvtvgpgllgvstlgpkrnsmvldvafvlegsdkigeadfnrskefmeeviqrmdvgqdsi hvtvlgysymvtveypfseaqskgdilqrvreiryqggnrtntglalrylsdhsflvsqgdreqapnlvymvtgnpasdeikrlpgdi qvvpigvgpnanvqelerigwpnapiliqdfetlpreapdlvlqrccsgeglqiptlspapdcsqpldvillldgsssfpasyfdemks fakafiskanigprltqvsvlqygsittidvpwnvvpekahllsvdvmgreggpsqigdalgfavryltsemhgarpgaskavvilvt dvsvdsvdaaadaarsnrvtvfpigigdrydaaglrilagpagdsnvvklqriedlptmvtlgnsflhklcsgfvricmdedgnekrp gdvwtlpdgchtvtcqpdgqtllkshrvncdrglrpscpnsgspvkveetcgcrwtcpcvctgsstrhivtfdgqnfkltgscsyvlfq -continued nkeqdlevilhngacspgarqgcmksievkhsalsvelhsdmevtvngrlvsvpyvggnmevnvygaimhevrfnhlghiftft pqnnefqlqlspktfasktyglcgicdengandfmlrdgtvttdwktlvqewtvgrpgqtcqpileeqclvpdsshcqvlllplfaech kv vWF497-716-R545A (SEQ ID NO 28)

edisepplhdfycsrlldlvflldgssrlseaefevlkafvvdmmerlaisqkwvrvavveyhdgshayiglkdrkrpsel rriasqvkyagsqvastsevlkytlfqifskidrpeasriallmasqepqrmsrnfvryvqglkkkvivipvgigphanlkqirliekq apenkafvlssvdeleqqrdeivsylcdlapeappptlppdmaqvtvg vWF binding protein (SEQ ID NO 29)

npelkdfneeeqlkcdlelnklenqilmlgktfygnyrddveslyskldlimgykdeerankkavnkrmlenkkedletiideffsdid ktrpnnipvledekqeeknhknmaqlksdteaaksdeskrskrskrslntqnhkpasqevseqqkaeydkraeerkarfldnq kikktpvvsleydfehkqridnendkklvvsaptkkptspttytetttqvpmptverqtqqqiiynapkglaglngeshdftttthqsptt snhthnn hCG C-terminus (SEQ ID NO 30)

sssskapppslpspsrlpgpsdtpilpq

F10AP (SEQ ID NO 31)

svaqatsssgeapdsitwkpydaadldptenpfdlldfnqtqpergdnnl

Example 3

Transient Expression of FVIII Frameworks and Fusion Proteins

HKB11 cells at a density of 0.9-1.1×$10^6$ are transfected with a complex of plasmid 0.7 mg/l and the transfection agent, 293Fectin (Invitrogen) 1.4 ml/l. The transfection complex is prepared by diluting the plasmid and the transfection separately in OPTIMEM (Invitrogen), mixing of the two solutions, and incubation of the mixture at room temperature for 20 minutes. The complex mixture is added to the cell suspension and the suspension is incubated in shaker incubator for 5 days at 36.5° C. and 5% $CO_2$. The cell culture harvest is filtered on a 0.22 μm membrane filter. FVIII frameworks and fusion proteins are purified from the cell culture harvest as described in Example 5.

Example 4

Stable Cell Expressing Fusion Protein

Serum-free adapted CHO-DUKX-B11 cells were transfected with an expression plasmid encoding the F8-500-albumin-Δa3 fusion protein. Transfected cells were selected with the dihydrofolate reductase system and cloned by limiting dilution. Clones were screened for FVIII production by ELISA and chromogenic activity assay. The clone JsJHOO9 was selected for upscaling. The cells were transferred to a bioreactor. The F8-500-albumin-Δa3 fusion was purified from cell culture harvests as described in Example 5.

Example 5

Purification of FVIII Frameworks and Fusion Proteins

A column was packed with the resin VIIISelect (GE Healthcare), with the dimensions 1.6 cm in diameter and 4 cm in bed height giving 8 mL, and was equilibrated with 20 mM Imidazol+10 mM $CaCl_2$+0.01% Tween80+250 mM NaCl, pH7.3 at 500 cm/h. The culture filtrate prepared as described in Example 3 was applied to the column, and the column was subsequently washed with first equilibration buffer and then 20 mM Imidazol+10 mM $CaCl_2$+0.01% Tween80+1.5M NaCl, pH7.3. The bound FVIII was eluted isocratic at 90 cm/h with 20 mM Imidazol+10 mM $CaCl_2$+0.01% Tween80+2.5 M NaCl+6.5M Propylenglycol, pH7.3. The fractions containing FVIII were pooled and diluted 1:10 with 20 mM Imidazol+10 mM $CaCl_2$+0.01% Tween80, pH7.3 and applied to a column packed with F25-Sepharose (Thim et al., Haemophilia, 2009). The column dimension was 1.6 cm in diameter and 2 cm in bed height giving 4 mL in column volume. The column was equilibrated at 180 cm/h with 20 mM Imidazol+10 mM $CaCl_2$+0.01% Tween80+150 mM NaCl+1M Glycerol, pH7.3 prior to application. After application the column was washed first with equilibration buffer and then 20 mM Imidazol+10 mM $CaCl_2$+0.01% Tween80+650 mM NaCl, pH7.3. The bound FVIII was isocratic eluted with 20 mM Imidazol+10 mM $CaCl_2$+0.01% Tween80+2.5M NaCl+50% (v/v) Ethylenglycol, pH7.3 at 30 cm/h. The fractions containing FVIII were pooled and diluted 1:15 with 20 mM Imidazol+10 mM $CaCl_2$+0.01% Tween80, pH7.3, except FVIII-variants with deletions of the a3 domain which were diluted 1:45 in the same buffer. The diluted pool was applied to a column packed with Poros 50HQ (PerSeptive Biosystem), with the column dimensions 0.5 cm in diameter and 5 cm in bed height giving 1 mL in column volume. The column was equilibrated at 300 cm/h with 20 mM Imidazol+10 mM $CaCl_2$+0.01% Tween80+50 mM NaCl+1M Glycerol, pH7.3 prior to application. The column was washed with equilibration buffer before the elution using a linear gradient over 5 column volumes from equilibration buffer to 20 mM Imidazol+10 mM $CaCl_2$+0.01% Tween80+μM NaCl+1M Glycerol, pH7.3. The fractions containing FVIII were pooled and the pool was stored at −80° until use. A table of yields over a typical purification is shown in Table 11.

The FVIII-variants with HIS-tag was purified essentially as described above, however the second purification step (F25-sepharose) was exchanged to Chelating Sepharose FF (GE Healtcare) charged with 2 column volumes of 1M $NiSO_4$. The column dimension was 0.5 cm in diameter and 5 cm bed height giving 1 mL column volume. The column was equilibrated with 30 mM Imidazol+10 mM $CaCl_2$+0.01% Tween80+1.5M NaCl, pH7.3 at 180 cm/h prior to application. After application the column was washed with 30 column volumes of equilibration buffer prior to elution using a linear gradient over 5 column volumes to 250 mM Imidazol+10 mM $CaCl_2$+0.01% Tween80+1.5M NaCl, pH7.3. The fractions containing FVIII were pooled and diluted 1:30 with 20 mM Imidazol+10 mM $CaCl_2$+0.01% Tween80, pH7.3. The final purification step (Poros 50HQ) was performed as described above.

Example 6

FVIII:C in Cell Culture Harvests Measured by Chromogenic Assay

The FVIII activity (FVIII:C) of the rFVIII compound in cell culture harvest (supernatant fraction) was evaluated in a chromogenic FVIII assay using Coatest SP reagents (Chromogenix) as follows: rFVIII samples and a FVIII standard (Coagulation reference, Technoclone) were diluted in Coatest assay buffer (50 mM Tris, 150 mM NaCl, 1% BSA, pH 7.3, with preservative). Fifty .mu.l of samples, standards, and buffer negative control were added to 96-well microtiter plates (Spectraplates MB, PERKIN ELMER®). All samples were tested diluted 1:100, 1:400, 1:1600, and 1:6400. The factor IXa/factor X reagent, the phospholipid reagent and CaCl.sub.2 from the Coatest SP kit were mixed 5:1:3 (vol:vol:vol) and 75 .mu.l of this added to the wells. After 15 min incubation at room temperature, 50 .mu.l of the factor Xa substrate S-2765/thrombin inhibitor I-2581 mix was added and the reactions were incubated 5 min at room temperature before 25 .mu.l 1 M citric acid, pH 3, was added. The absorbance at 405 nm was measured on an Envision microtiter plate reader (PERKIN ELMER®) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by ELISA. The results are shown in Table 1-10.

Example 7

Purification of FVIII Frameworks and Fusion Proteins

F8-500-albumin-Δa3 purified as described in Example 5 (13 mg, 6.5 mg/ml) in a buffer consisting of: imidazol (20 mM), calcium chloride (10 mM), Tween 80 (0.02%), sodium chloride (500 mM), and glycerol (1 M) in water (pH 7.3, was thawed.

Nine microgram sialidase from *Arthrobacter ureafaciens* (1.9 U, in 7 microliter buffer), 280 microgram sialyl tranferase (in 112 microliter, His-ST3Gal-1, 2.5 mg/ml, EC 2.4.99.4, WO 2006102652), and 59 milligram cytidine monophospate N-5'-PEG-glycerol-neuraminic acid (in 290 microliter, see WO2007/056191) were added, and pH was adjusted to 6.9 using HCl (1M). The final volume was 2.7 mL. The resulting mixture was then left for 22 hours at 22-25 degrees Celsius (room temperature).

After glycopegylation, the mixture was diluted to 50 ml with Buffer A (Tris (25 mM), calcium chloride (10 mM), Tween80 (0.02%), and glycerol (1 M) in water, pH 7.5). The deluted mixture was loaded onto a Source30Q column (GE Healthcare Bio-Sciences, HiHerod, Denmark, column volume 1.1 mL). The immobilised material was then washed with Buffer A (4 column volumes) and subsequently eluted from the column using a gradient of 0-100% Buffer B (Tris (25 mM), calcium chloride (10 mM), Tween 80 (0.02%), sodium chloride (0.7 M), and glycerol (1 M) in water, pH 7.5). Gradient: 8 CV 5-10% Buffer B, 13.5 CV 10-100% Buffer B, and 3 CV 100% Buffer B.

The early eluting 2.5 mL peak fraction was mixed with 1.2 milligram cytidine monophospate N-5' acetyl-neuraminic acid (in 12 microliter) and 62 microgram sialyltransferase (in 52 microliter, MBP-SBD-ST3Gal-III, EC 2.4.99.6, see WO 2006102652).

The mixture was left for 22 hours at 22-25 degrees Celsius (room temperature), and subsequently loaded onto a Superdex200 pg column (GE Healthcare Bio-Sciences, Hillerød, Denmark; column volume 120 ml). Product was then eluted using a buffer consisting of: L-histidine (1.5 g/L), L-methionine (55 mg/L), calcium chloride (250 mg/L), Tween 80 (0.1 g/L), sodium chloride (18 g/L), and sucrose (1.5 g/L) in water, pH 6.9. The first product-containing fractions (12 mL) were isolated and pooled; product concentration was approximately 0.06 mg/mL.

Finally, the product was concentrated by centrifugation in an Amicon Centriprep YM-50 (cutoff: 50 kDa). The volume after concentration was 1.7 mL, containing 0.35 mg/mL glycopegylated F8-500-albumin-Δa3 (purity>90%). This compound is referred to in Table 12 as 40K-PEG-O-F8-500-albumin-Δa3.

Example 8

FVIII:C in Purified Samples Measured by Chromogenic Assay

The FVIII activity (FVIII:C) of the purified rFVIII compound (isolated as disclosed in Example 5) was evaluated in a chromogenic FVIII assay using Coatest SP reagents (Chromogenix) as follows: rFVIII samples and a FVIII standard (e.g. purified wild-type rFVIII calibrated against the 7th international FVIII standard from NIBSC) were diluted in Coatest assay buffer (50 mM Tris, 150 mM NaCl, 1% BSA, pH 7.3, with preservative). Fifty .mu.l of samples, standards, and buffer negative control were added to 96-well microtiter plates (Nunc) in duplicates. The factor IXa/factor X reagent, the phospholipid reagent and CaCl.sub.2 from the Coatest SP kit were mixed 5:1:3 (vol:vol:vol) and 75 .mu.l of this added to the wells. After 15 min incubation at room temperature 50 .mu.l of the factor Xa substrate S-2765/thrombin inhibitor I-2581 mix was added and the reactions incubated 10 min at room temperature before 25 .mu.l 1 M citric acid, pH 3, was added. The absorbance at 415 nm was measured on a Spectramax microtiter plate reader (MOLECULAR DEVICES®) with absorbance at 620 nm used as reference wavelength. The value for the negative control was subtracted from all samples and a calibration curve prepared by linear regression of the absorbance values plotted vs. FVIII concentration. The specific activity was calculated by dividing the activity of the samples with the protein concentration determined by HPLC. For HPLC, the concentration of the sample was determined by integrating the area under the peak in the chromatogram corresponding to the light chain and compare with the area of the same peak in a parallel analysis of a wild-type rFVIII, where the concentration was determined by amino acid analyses. The results are shown in Table 1-10.

Example 9

FVIII:C in Purified Samples Measured by One-Stage Clot Assay

FVIII:C of the rFVIII compounds was further evaluated in a one-stage FVIII clot assay as follows: rFVIII samples and a FVIII standard (e.g. purified wild-type rFVIII calibrated against the 7th international FVIII standard from NIBSC) were diluted in HBS/BSA buffer (20 mM hepes, 150 mM NaCl, pH 7.4 with 1% BSA) to approximately 10 µml followed by 10-fold dilution in FVIII-deficient plasma containing VWF (Dade Behring). The samples were subsequently diluted in HBS/BSA buffer. The APTT clot time was measured on an ACL300R or an ACL5000 instrument (Instrumentation Laboratory) using the single factor program. FVIII-deficient plasma with VWF (Dade Behring) was used as assay plasma and SynthASil, (HemosIL™, Instrumentation Laboratory) as aPTT reagent. In the clot instrument, the diluted sample or standard is mixed with FVIII-deficient plasma, aPTT reagents at 37° C. Calcium chloride is assed and time until clot formation is determined by turbidity. The FVIII:C in the sample is calculated based on a standard curve of the clot formation times of the dilutions of the FVIII standard. The results are shown in Table 1-10.

Example 10

Pharmacokinetics of FVIII Frameworks and Fusion Proteins in FVIII- and VWF-Deficient Mice The phamacokinetics of rFVIII variants were evaluated in FVIII-deficient mice (FVIII exon 16 knock out (KO) mice with C57Bl/6 background, bred at Taconic M&B) or in vWF-deficient mice (vWF exon 4+5 KO mice with C57Bl/6 background bred at Charles River, Germany). The vWF-KO mice had 13% of normal FVIII:C (see example 6), while the FVIII-KO mice had no detectable FVIII:C. A mixture of male and female (approximately 1:1) with an approximate weight of 25 grams and age range of 16-28 weeks were used. The mice received a single i.v. injections of rFVIII (280 IU/kg) in the tail vein. Blood was taken from the orbital plexus at time points up to 64 hours after dosing using non-coated capillary glass tubes. Three samples were taken from each mouse, and 2 to 4 samples were collected at each time point. Blood was immediately stabilized with sodium citrate and diluted in four volumes FVIII Coatest SP buffer (see example 6) before 5 min centrifugation at 4000×g. Plasma obtained from diluted blood was frozen on dry ice and kept at −80° C. The FVIII:C was determined in a chromogenic assay as described in example 6 Pharmacokinetic analysis was carried out by non-compartmental methods (NCA) using WinNonlin Pro version 4.1 software. Results are shown in Table 12. The fold prolongation of fusion protein is calculated by dividing the half-life of the fusion protein with that of the FVIII framework without the fusion partner.

Example 11

Analysis of Fusion Protein Binding to Platelets

Platelet-binding of a fusion protein can be tested by flow cytometry. Peripheral blood platelets may be purified, or whole blood can be used. The platelets may be activated or resting. The platelets are incubated with fusion protein for 15-30 min. The fusion protein may be directly labelled with a fluorophore or detected using a fluorescently labelled secondary antibody.

A fluorescently labelled platelet specific antibody not interfering with binding of the fusion protein can be added to assess whether the particles binding the fusion protein are indeed platelets. After incubation, the cells are washed to remove fusion protein, and the samples are analyzed on a flow cytometer. The flow cytometer detects unlabelled cells and fluorescently labelled molecules binding to cells and thus can be used to specifically analyze to which extent fusion protein is bound to platelets (or other cells).

The specificity of binding can be assessed e.g. by adding a surplus of unlabelled antibody (when using directly labelled fusion protein). Binding of the FVIII moiety to the platelets can be assessed e.g. by adding a surplus of annexin V or FVIII.

Internalization of the fusion protein by the resting platelet may be assessed e.g. by incubating platelets with directly labelled fusion protein followed by incubation with an antibody, which quenches the signal from surface-bound (i.e. not internalized) fusion protein. Only the internalized fusion protein will then be detected by flow cytometry. It may hypothesized that activated platelets will release internalized fusion-protein at the site of clot formation.

Example 12

Pharmacokinetics of GPIIIa-Targeted Fusion Proteins in GPIIIa Transgenic Mice The GPIIIa-targeted fusion protein binds to the human GPIIb/IIIa (integrin a2b3) receptor on platelets, but it may not recognize murine GPIIb/IIIa, preventing the use of wild type mice for pharmacokinetic analyses. The pharmacokinetic profile of GPIIIa-targeted fusion proteins can be analyzed in transgenic mice expressing human GPIIIa, which associates with murine GPIIb enabling the binding of fusion protein to the receptor. Fusion protein will be injected intravenously to GPIIIa transgenic mice and blood collected at various timepoints after injection (e.g. 0.5, 24, 72, 288 hours). The injected fusion protein (free and/or platelet-bound) may be quantified by means of an ELISA or the fusion protein may be radioactively or fluorescently labelled and detected.

TABLE 1

BDD FVIII frameworks that can constitute the FVIII part of fusion proteins

| Name | FVIII part | Fusion partner | Position of fusion partner | Specific activity (mU/ng)* |
|---|---|---|---|---|
| F8-500 | F8-500 | n.a | n.a | 17.9/17.0 |
| F8-500-Δa3 | F8-500-Δa3 | n.a | n.a | 13.6/13.8 |
| F8-500-His | F8-500-His | n.a. | n.a. | 12.1/8.1 |
| F8-500-Δa3-His | F8-500-Δa3-His | n.a. | n.a. | n.d./n.d. |
| F8-500-Y1680F | F8-500-Y1680F | n.a. | n.a. | 16.6**/n.d |
| F8-500-Y1680C | F8-500-Y1680C | n.a. | n.a. | 19.7/n.d. |

*Chromogenic assay/clot assay
**Measured in cell culture harvest (high values may represent poor detection by ELISA)

TABLE 2

| | | | | Specific |
|---|---|---|---|---|
| Name | FVIII part | Fusion partner | Position of fusion partner | activity (mU/ng) |
| F8-500-hFc(IgG1) | F8-500 | hFc | In B domain | 19.9**/n.d. 14.1**/n.d. |
| F8-500-hFc(IgG1)-His | F8-500-His | hFc | In B domain | |
| F8-500-Y1680F-hFc(IgG1) | F8-500-Y1680F | hFc | In B domain | |
| F8-500-Y1680C-hFc(IgG1) | F8-500-Y1680C | hFc | In B domain | |
| F8-500-hFc(IgG1)-Δa3 | F8-500-Δa3 | hFc | At a3s position | 6.0**/n.d. 28.5**/n.d. |
| F8-500-C2 linked-(GGGS)6-hFc(IgG1) | F8-500 | hFC | At C-terminus of LC | 16.7**/n.d. |
| F8-500-C2 linked-GS-hFc(IgG1) | F8-500 | hFC | At C-terminus of LC | 14.4**/n.d. |
| F8-500-C2 linked-hFc(IgG1) (F8-500-hFC-LC) | F8-500 | hFC | At C-terminus of LC | 13.4**/n.d. |
| F8-500-Y1680F-C2-linked-hFc(IgG1) (F8-500-Y1680F-hFC-LC) | F8-500-Y1680F | hFC | At C-terminus of LC | |
| F8-500-Y1680C-C2-linked-hFc(IgG1) (F8-500-Y1680C-hFC-LC) | F8-500-Y1680C | hFC | At C-terminus of LC | |
| F8-500-mFc(IgG2A) | F8-500 | mFc | In B domain | 18.5**/n.d. 13.9**/n.d. |
| F8-500-mFc(IgG2A)-His | F8-500-His | mFc | In B domain | |
| F8-500-Y1680F-mFc(IgG2A) | F8-500-Y1680F | mFc | In B domain | |
| F8-500-Y1680C-mFc(IgG2A) | F8-500-Y1680C | mFc | In B domain | |
| F8-500-mFc(IgG2A)-Δa3 | F8-500-Δa3 | mFc | At a3s position | |
| F8-500-C2 linked-(GGGS)6-mFc(IgG2A) | F8-500 | mFC | At C-terminus of LC | 15.5**/n.d. |
| F8-500-C2 linked-GS-mFc(IgG2A) | F8-500 | mFC | At C-terminus of LC | 15.2**/n.d. |
| F8-500-C2 linked-mFc(IgG2A) | F8-500 | mFC | At C-terminus of LC | 12.9**/n.d |
| F8-500-Y1680F-C2-linked-mFc(IgG2A) | F8-500-Y1680F | mFC | At C-terminus of LC | |
| F8-500-Y1680C-C2-linked-mFc(IgG2A) | F8-500-Y1680C | mFC | At C-terminus of LC | |
| F8-500-albumin | F8-500 | HSA | In B domain | 14.7/n.d. |
| F8-500-albumin-His | F8-500-His | HSA | In B domain | 8.1/6.2 |
| F8-500-Albumin-S727P | F8-500 | HSA | In B domain | 12.3**/n.d. |
| F8-500-Y1680F-albumin | F8-500-Y1680F | HSA | In B domain | |
| F8-500-Y1680C-albumin | F8-500-Y1680C | HSA | In B domain | |
| F8-500-albumin-Δa3 | F8-500-Δa3 | HSA | At a3s position | 2.0/n.d. |
| F8-500-C2 linked-(GGGS)6-albumin | F8-500 | HSA | At C-terminus of LC | 22.7**/n.d. |
| F8-500-C2 linked-GS-albumin | F8-500 | HSA | At C-terminus of LC | 17.7**/n.d. |

TABLE 2-continued

Fusion proteins interacting with FcRn

| Name | FVIII part | Fusion partner | Position of fusion partner | Specific activity (mU/ng) |
|---|---|---|---|---|
| F8-500-C2 linked-albumin (F8-500-albumin-LC) | F8-500 | HSA | At C-terminus of LC | |
| F8-500-Y1680F-C2-linked-albumin (F8-500-Y1680F-albumin-LC) | F8-500-Y1680F | HSA | At C-terminus of LC | |
| F8-500-Y1680C-C2-linked-albumin (F8-500-Y1680C-albumin-LC) | F8-500-Y1680C | HSA | At C-terminus of LC | |
| F8-500-transferrin | F8-500 | Transferrin | In B domain | |
| F8-500-transferrin-His | F8-500-His | Transferrin | In B domain | |
| F8-500-Y1680F-transferrin | F8-500-Y1680F | Transferrin | In B domain | |
| F8-500-Y1680C-transferrin | F8-500-Y1680C | Transferrin | In B domain | |
| F8-500-transferrin-Δa3 | F8-500-Δa3 | Transferrin | At a3s position | |
| F8-500-C2 linked-transferrin (F8-500-transferrin-LC) | F8-500 | Transferrin | At C-terminus of LC | |
| F8-500-Y1680F-C2-linked-transferrin (F8-500-Y1680F-transferrin-LC) | F8-500-Y1680F | Transferrin | At C-terminus of LC | |
| F8-500-Y1680C-C2-linked-transferrin (F8-500-Y1680C-transferrin-LC) | F8-500-Y1680C | Transferrin | At C-terminus of LC | |

*Chromogenic assay/clot assay
**Measured in cell culture harvest (high values may represent poor detection by ELISA)

TABLE 3

Fusion proteins interacting with immunoglobulins

| Name | FVIII part | Fusion partner | Position of fusion partner | Specific activity (mU/ng)* |
|---|---|---|---|---|
| F8-500-hFcγRI | F8-500 | hFcγRI (CD64) | In B domain | 22.2/20.0 |
| F8-500-hFcγRI-His | F8-500-His | hFcγRI (CD64) | In B domain | 11.6/4.9 |
| F8-500-Y1680F-hFcγRI | F8-500-Y1680F | hFcγRI (CD64) | In B domain | |
| F8-500-Y1680C-hFcγRI | F8-500-Y1680C | hFcγRI (CD64) | In B domain | |
| F8-500-hFcγRI-Δa3 | F8-500-Δa3 | hFcγRI (CD64) | At a3s position | 5.3/n.d. |
| F8-500-C2-linked-hFcγRI (F8-500-hFcγRI-LC) | F8-500 | hFcγRI (CD64) | At C-terminus of LC | |
| F8-500-Y1680F-C2-linked-hFcγRI (F8-Y1680F-500-hFcγRI-LC) | F8-500-Y1680F | hFcγRI (CD64) | At C-terminus of LC | |
| F8-500-Y1680C-C2-linked-hFcγRI (F8-500-Y1680C-hFcγRI-LC) | F8-500-Y1680C | hFcγRI (CD64) | At C-terminus of LC | |
| F8-500-FcRn | F8-500 | FcRn | In B domain | 27.2**/n.d. |

TABLE 3-continued

Fusion proteins interacting with immunoglobulins

| Name | FVIII part | Fusion partner | Position of fusion partner | Specific activity (mU/ng)* |
|---|---|---|---|---|
| F8-500-FcRn-H166K | F8-500 | FcRn | In B domain | 20.8**/n.d. |

*Chromogenic assay/clot assay
**Measured in cell culture harvest (high values may represent poor detection by ELISA)

TABLE 4

Fusion proteins with the capability of reducing interaction with clearance receptors

| Name | FVIII part | Fusion partner | Position of fusion partner | Specific activity (mU/ng)* |
|---|---|---|---|---|
| F8-500-LRP-CR5-6 | F8-500 | LRP CR5-6 | In B domain | 14.2/n.d. |
| F8-500-LRP-CR5-6-His | F8-500-His | LRP CR5-6 | In B domain | |
| F8-500-LRP-CR6-7 | F8-500 | LRP CR6-7 | In B domain | 9.5**/n.d. |
| F8-500-LRP-CR6 | F8-500 | LRP CR6 | In B domain | 8.9**/n.d. |

*Chromogenic assay/clot assay

**Measured in cell culture harvest (high values may represent poor detection by ELISA)

TABLE 5

| Fusion proteins binding to platelets | | | | |
|---|---|---|---|---|
| Name | FVIII part | Fusion partner | Position of fusion partner | Specific activity (mU/ng)* |
| F8-500-anti-GPIIIa-1-HC-LC | F8-500 | SC anti-GPIIIa-1-HC-LC | In B domain | 29.3**/n.d. |
| F8-500-linker-anti-GPIIIa-1-HC-LC | F8-500 | SC anti-GPIIIa-1-HC-LC | In B domain | 40.3**/n.d. |
| F8-500-SC anti-GPIIIa-2-HC-LC | F8-500 | SC anti-GPIIIa-2-HC-LC | In B domain | 22.5**/n.d. |
| F8-500-SC anti-GPIIIa-2-HC-LC-His | F8-500-His | SC anti-GPIIIa-2-HC-LC | In B domain | — |
| F8-500-linker-SC anti-GPIIIa-2-HC-LC-His | F8-500-His | SC anti-GPIIIa-2-HC-LC | In B domain | 45.9**/n.d. |
| F8-500-Δa3-SC anti-GPIIIa-2-HC-LC-His | F8-500-Δa3-His | SC anti-GPIIIa-2-HC-LC | In B domain | — |
| F8-500-Y1680F-SC anti-GPIIIa-2-HC-LC | F8-500-Y1680F | SC anti-GPIIIa-2-HC-LC | In B domain | |
| F8-500-Y1680C-SC anti-GPIIIa-2-HC-LC | F8-500-Y1680C | SC anti-GPIIIa-2-HC-LC | In B domain | |

TABLE 5-continued

| Fusion proteins binding to platelets | | | | |
|---|---|---|---|---|
| Name | FVIII part | Fusion partner | Position of fusion partner | Specific activity (mU/ng)* |
| F8-500-SC anti-GPIIIa-2-HC-LC-Δa3 | F8-500-Δa3 | SC anti-GPIIIa-2-HC-LC | At a3s position | 26.2**/n.d. |
| F8-500-C2-linked-SC anti-GPIIIa-2-HC-LC (F8-500-SC anti-GPIIIa-2-HC-LC-LC) | F8-500 | SC anti-GPIIIa-2-HC-LC | At C-terminus of LC | |
| F8-500-Y1680F-C2-linked-SC anti-GPIIIa-2-HC-LC (F8-500-Y1680F-SC anti-GPIIIa-2-HC-LC-LC) | F8-500-Y1680F | SC anti-GPIIIa-2-HC-LC | At C-terminus of LC | |
| F8-500-Y1680C-C2-linked-SC anti-GPIIIa-2-HC-LC (F8-500-Y1680C-SC anti-GPIIIa-2-HC-LC-LC) | F8-500-Y1680C | SC anti-GPIIIa-2-HC-LC | At C-terminus of LC | |
| F8-500-SC anti-GPIIIa-2-LC-HC | F8-500 | SC anti-GPIIIa-2-LC-HC | In B domain | 28.3**/n.d. |
| F8-500-SC anti-GPIIIa-2-LC-HC | F8-500 | SC anti-GPIIIa-2-LC-HC | In B domain | 95.4**/n.d. |
| F8-500-linker-SC anti-GPIIIa-2-LC-HC-His | F8-500-His | SC anti-GPIIIa-2-LC-HC | In B domain | 47.5**/n.d. |
| F8-500-Δa3-SC anti-GPIIIa-2-LC-HC-His | F8-500-Δa3-His | SC anti-GPIIIa-2-LC-HC | In B domain | 81.4**/n.d. |
| F8-500-Y1680F-SC anti-GPIIIa-2-LC-HC | F8-500-Y1680F | SC anti-GPIIIa-2-LC-HC | In B domain | |
| F8-500-Y1680C-SC anti-GPIIIa-2-LC-HC | F8-500-Y1680C | SC anti-GPIIIa-2 (LC-HC) | In B domain | |
| F8-500-SC anti-GPIIIa-2-LC-HC-Δa3 | F8-500-Δa3 | SC anti-GPIIIa-2-LC-HC | At a3s position | 29.2**/n.d. |
| F8-500-C2-linked-(GGGS)6-SC anti-GPIIIa-2-LC-HC (F8-500-SC anti- | F8-500 | SC anti-GPIIIa-2-LC-HC | At C-terminus of LC | 22.4**/n.d. |

TABLE 5-continued

Fusion proteins binding to platelets

| Name | FVIII part | Fusion partner | Position of fusion partner | Specific activity (mU/ng)* |
|---|---|---|---|---|
| GPIIIa-2-LC-HC-LC) | | | | |
| F8-500-Y1680F-C2-linked-SC anti-GPIIIa-2-LC-HC (F8-500-Y1680F-SC anti-GPIIIa-2-LC-HC-LC) | F8-500-Y1680F | SC anti-GPIIIa-2-LC-HC | At C-terminus of LC | |
| F8-500-Y1680C-C2-linked-GS-SC anti-GPIIIa-2-LC-HC (F8-500-y1680C-SC anti-GPIIIa-2-LC-HC-LC) | F8-500-Y1680C | SC anti-GPIIIa-2-LC-HC | At C-terminus of LC | 16.6**/n.d. |

*Chromogenic assay/clot assay
**Measured in cell culture harvest (high values may represent poor detection by ELISA)

TABLE 6

Fusion proteins interacting with serum albumin

| Name | FVIII part | Fusion partner | Position of fusion partner | Specific activity (mU/ng)* |
|---|---|---|---|---|
| F8-500-ABD035 | F8-500 | Albumin binding peptide ABD035 | In B domain | |
| F8-500-ABD035-His | F8-500-His | Albumin binding peptide ABD035 | In B domain | 8.3/n.d. |
| F8-500-Y1680F-ABD035 | F8-500-Y1680F | Albumin binding peptide ABD035 | In B domain | |
| F8-500-Y1680C-ABD035 | F8-500-Y1680C | Albumin binding peptide ABD035 | In B domain | |
| F8-500-ABD035-Δa3 | F8-500-Δa3 | Albumin binding peptide ABD035 | At a3s position | 4.0/0.5 |
| F8-500-C2-linked-ABD035 (F8-500-ABD035-LC) | F8-500 | Albumin binding peptide ABD035 | At C-terminus of LC | |
| F8-500-Y1680F-C2-linked ABD035 (F8-500-Y1680F-ABD035-LC) | F8-500-Y1680F | Albumin binding peptide ABD035 | At C-terminus of LC | |
| F8-500-Y1680C-C2-linked ABD035 (F8-500-Y1680C-ABD035-LC) | F8-500-Y1680C | Albumin binding peptide ABD035 | At C-terminus of LC | |
| F8-500-4XABD035 | F8-500 | 4 X Albumin binding peptide ABD035 | In B domain | 14.8/n.d. |
| F8-500-4XABD035-His | F8-500-His | 4 X Albumin binding peptide ABD035 | In B domain | |
| F8-500-Y1680F-4X ABD035 | F8-500-Y1680F | 4 X Albumin binding peptide ABD035 | In B domain | |
| F8-500-Y1680C-4X ABD035 | F8-500-Y1680C | 4 X Albumin binding peptide ABD035 | In B domain | |
| F8-500-4X ABD035-Δa3 | F8-500-Δa3 | 4 X Albumin binding peptide ABD035 | At a3s position | |

TABLE 6-continued

Fusion proteins interacting with serum albumin

| Name | FVIII part | Fusion partner | Position of fusion partner | Specific activity (mU/ng)* |
|---|---|---|---|---|
| F8-500-C2-linked-4X ABD035 (F8-500-4X ABD035-LC) | F8-500 | 4 X Albumin binding peptide ABD035 | At C-terminus of LC | |
| F8-500-Y1680F-C2-linked-4X ABD035 (F8-500-Y1680F-4X ABD035-LC) | F8-500-Y1680F | 4 X Albumin binding peptide ABD035 | At C-terminus of LC | |
| F8-500-Y1680C-C2-linked-4X ABD035 (F8-500-Y1680C-4X ABD035-LC) | F8-500-Y1680C | 4 X Albumin binding peptide ABD035 | At C-terminus of LC | |
| F8-500-SC anti-HSA | F8-500 | SC anti-HSA | In B domain | |
| F8-500-SC anti-HSA-His | F8-500-His | SC anti-HSA | In B domain | |
| F8-500-Y1680F-SC anti-HSA | F8-500-Y1680F | SC anti-HSA | In B domain | |
| F8-500-Y1680C-SC anti-HSA | F8-500-Y1680C | SC anti-HSA | In B domain | |
| F8-500-SC anti-HSA-Δa3 | F8-500-Δa3 | SC anti-HSA | At a3s position | |
| F8-500-C2-linked-SC anti-HSA (F8-500-SC anti-HSA-LC) | F8-500 | SC anti-HSA | At C-terminus of LC | |
| F8-500-Y1680F-C2-linked-SC anti-HSA (F8-500-Y1680F-SC anti-HSA-LC) | F8-500-Y1680F | SC anti-HSA | At C-terminus of LC | |
| F8-500-Y1680C-C2-linked-SC anti-HSA (F8-500-Y1680C-SC anti-HSA-LC) | F8-500-Y1680C | SC anti-HSA | At C-terminus of LC | |

*Chromogenic assay/clot assay
**Measured in cell culture harvest (high values may represent poor detection by ELISA)

TABLE 7

Fusion proteins shielding the molecule from clearance receptors

| Name | FVIII part | Fusion partner | Position of fusion partner | Specific activity (mU/ng)* |
|---|---|---|---|---|
| F8-500-Seq A | F8-500 | Sequence A | In B domain | |
| F8-500-Seq A-His | F8-500-His | Sequence A | In B domain | 19.2**/n.d. |
| F8-500-Y1680F-Seq A | F8-500-Y1680F | Sequence A | In B domain | |
| F8-500-Y1680C-Seq A | F8-500-Y1680C | Sequence A | In B domain | |
| F8-500-Seq A-Δa3 | F8-500-Δa3 | Sequence A | At a3s position | |
| F8-500-C2-linked-Seq A (F8-500-Seq A-LC) | F8-500 | Sequence A | At C-terminus of LC | |

TABLE 7-continued

Fusion proteins shielding the molecule from clearance receptors

| Name | FVIII part | Fusion partner | Position of fusion partner | Specific activity (mU/ng)* |
|---|---|---|---|---|
| F8-500-Y1680F-C2-linked Seq A (F8-500-Y1680F-Seq A-LC) | F8-500-Y1680F | Sequence A | At C-terminus of LC | |
| F8-500-Y1680C-C2-linked Seq A (F8-500-Y1680C-Seq A-LC) | F8-500-Y1680C | Sequence A | At C-terminus of LC | |
| F8-500-ELP80 | F8-500 | ELP80 | In B domain | |
| F8-500-ELP80-His | F8-500-His | ELP80 | In B domain | 13.8**/n.d. |
| F8-500-Y1680F-ELP80 | F8-500-Y1680F | ELP80 | In B domain | |
| F8-500-Y1680C-ELP80 | F8-500-Y1680C | ELP80 | In B domain | |
| F8-500-ELP80-Δa3 | F8-500-Δa3 | ELP80 | At a3s position | |
| F8-500-C2-linked-ELP80 | F8-500 | ELP80 | At C-terminus of LC | |
| F8-500-Y1680F-C2-linked-ELP80 | F8-500-Y1680F | ELP80 | At C-terminus of LC | |
| F8-500-Y1680C-C2-linked ELP80 | F8-500-Y1680C | ELP80 | At C-terminus of LC | |

*Chromogenic assay/clot assay
**Measured in cell culture harvest (high values may represent poor detection by ELISA)

TABLE 8

Fusion proteins with modulated affinity to vWF

| Name | FVIII part | Fusion partner | Position of fusion partner | Specific activity (mU/ng)* |
|---|---|---|---|---|
| F8-500-Extra a3 | F8-500 | Extra a3 | In B domain | 10.0**/n.d. |
| F8-500-Extra a3-His | F8-500-His | Extra a3 | In B domain | 7.7**/n.d. |
| F8-500-Y1680F-Extra a3 | F8-500-Y1680F | Extra a3 | In B domain | |
| F8-500-Y1680C-Extra a3 | F8-500-Y1680C | Extra a3 | In B domain | |
| F8-500-Extra a3-Δa3 | F8-500-Δa3 | Extra a3 | At a3s position | |
| F8-500-C2-linked-Extra a3 (F8-500-Extra a3-LC) | F8-500 | Extra a3 | At C-terminus of LC | |
| F8-500-Y1680F-C2-linked-Extra a3 (F8-500-Y1680F-Extra a3-LC) | F8-500-Y1680F | Extra a3 | At C-terminus of LC | |
| F8-500-Y1680C-C2-linked Extra a3 (F8-500-Y1680C-Extra a3-LC) | F8-500-Y1680C | Extra a3 | At C-terminus of LC | |

*Chromogenic assay/clot assay
**Measured in cell culture harvest (high values may represent poor detection by ELISA)

TABLE 9

Other fusion proteins

| Name | FVIII part | Fusion partner | Position of fusion partner | Specific activity (mU/ng)* |
|---|---|---|---|---|
| F8-500-GHBP | F8-500 | Growth hormone binding protein | In B domain | 22.8**/n.d. |
| F8-GHBP-His | F8-500-His | Growth hormone binding protein | In B domain | 7.6/4.5 |
| F8-500-FIX298-342 | F8-500 | AS 298-342 of FIX | In B domain | 12.3**/n.d. |
| F8-500-FIX47-125 | F8-500 | AS 47-125 of FIX | In B domain | 18.0/n.d. |
| F8-500-FIX47-125-His | F8-500-His | AS 47-125 of FIX | In B domain | 14.4/13.3 |
| F8-500-vWF1-272 | F8-500 | AS 1-272 of vWF | In B domain | 44.5**/n.d. |
| F8-500-vWF1-1390 | F8-500 | AS 1-1390 of vWF | In B domain | 16.0**/n.d. |
| F8-500-vWF497-716-R545A | F8-500 | AS 497-716 of vWF | In B domain | 11.5/8.8 |
| F8-500-vWF497-716-R545A-His | F8-500-His | AS 497-716 of vWF | In B domain | 256.9**/n.d. |

TABLE 9-continued

Other fusion proteins

| Name | FVIII part | Fusion partner | Position of fusion partner | Specific activity (mU/ng)* |
|---|---|---|---|---|
| F8-500-vWF binding protein | F8-500 | vWF-binding protein | In B domain | 19.8**/n.d. |
| F8-500-hCG C-terminus-His | F8-500-His | 28 C-terminal AS of hCG b-chain | In B domain | 11.4/n.d. |
| F8-500-hCG-C-terminus-Δa3 | F8-500-Δa3 | 28 C-terminal AS of hCG b-chain | At a3s position | 18.2/n.d. |
| F8-500-F10AP | F8-500 | Activation peptide of hFX | In B domain | 22.5**/n.d. |
| F8-500-F10AP-His | F8-500-His | Activation peptide of hFX | In B domain | 16.8/n.d. |
| F8-500-Y1680F-F10AP | F8-500-Y1680F | Activation peptide of hFX | In B domain | |
| F8-500-Y1680C-F10AP | F8-500-Y1680C | Activation peptide of hFX | In B domain | |
| F8-500-F10AP-Δa3 | F8-500-Δa3 | Activation peptide of hFX | At a3s position | |
| F8-500-C2-linked-F10AP (F8-500-F10AP-LC) | F8-500 | Activation peptide of hFX | At C-terminus of LC | |
| F8-500-Y1680F-C2-linked-F10AP (F8-500-Y1680F-F10AP-LC) | F8-500-Y1680F | Activation peptide of hFX | At C-terminus of LC | |
| F8-500-Y1680C-C2-linked-F10AP (F8-500-Y1680C-F10AP-LC) | F8-500-Y1680F | Activation peptide of hFX | At C-terminus of LC | |

*Chromogenic assay/clot assay
**Measured in cell culture harvest (high values may represent poor detection by ELISA)

TABLE 10

Fusion proteins with modulated affinity to lipids

| Name | FVIII part | Fusion partner | Position of fusion partner | Specific activity (mU/ng)* |
|---|---|---|---|---|
| F8-500-Extra C2 | F8-500 | Extra C2 | In B domain | |
| F8-500-Extra C2-His | F8-500-His | Extra C2 | In B domain | |
| F8-500-Y1680F-Extra C2 | F8-500-Y1680F | Extra C2 | In B domain | |
| F8-500-Y1680C-Extra C2 | F8-500-Y1680C | Extra C2 | In B domain | |
| F8-500-Extra C2-Δa3 | F8-500-Δa3 | Extra C2 | At a3s position | |
| F8-500-C2 linked-(GGGS)6-extra C2 | F8-500 | Extra C2 | At C-terminus of LC | 8.3**/n.d. |
| F8-500-C2-linked-GS-Extra C2 | F8-500 | Extra C2 | At C-terminus of LC | 7.7**/n.d. |

TABLE 10-continued

Fusion proteins with modulated affinity to lipids

| Name | FVIII part | Fusion partner | Position of fusion partner | Specific activity (mU/ng)* |
|---|---|---|---|---|
| F8-500-Y1680E-C2-linked-Extra C2 | F8-500-Y1680F | Extra C2 | At C-terminus of LC | |
| F8-500-Y1680C-C2-linked-Extra C2 | F8-500-Y1680C | Extra C2 | At C-terminus of LC | |

*Chromogenic assay/clot assay
**Measured in cell culture harvest (high values may represent poor detection by ELISA)

TABLE 11

Typical yields of the purification process described in Example 5

| Sample | Vol./mL | Activity/ U * mL$^{-1}$ | Yield/% Step | Yield/% Total |
|---|---|---|---|---|
| Culture filtrate | 1650 | 17 | 100 | 100 |
| Step1: Flow thru | 1650 | 3.5 | 21 | — |
| Step1: Eluate pool | 14 | 1021 | 51 | 51 |
| Step2: Flow thru | 133 | 19 | 17 | — |
| Step2: Eluate pool | 8 | 820 | 45 | 23 |
| Step3: Flow thru | 117 | 0.9 | 2 | — |
| Step3: Eluate pool | 1.5 | 3000 | 69 | 16 |

TABLE 12

In vivo half-lifes of FVIII frameworks and fusion proteins in FVIII- or vWF deficient mice

| Name | Half-life in FVIII-deficient mice (h)* | Fold prolongation in FVIII-deficient mice* | Half-life in vWF-deficient mice (h)* | Fold prolongation in vWF-deficient mice* |
|---|---|---|---|---|
| F8-500 | 4.5/8.6 | n.a. | n.d./0.3 | n.a. |
| F8-500-Δa3 | 0.3/0.3 | n.a. | n.d. | n.a. |
| F8-500-His | n.d. | n.a. | 0.1/0.1 | n.a. |
| F8-500-Δa3-His | n.d. | n.a. | n.d. | n.a. |
| F8-500-Y1680F | 0.5/n.d. | n.a. | n.d. | n.a. |
| F8-500-Y1680C | n.d. | n.a. | n.d. | n.a. |
| F8-500-hFc(IgG1)-Δa3 | 0.7/n.d. | 2.3/n.d. | n.d. | n.d |
| F8-500-C2 linked-(GGGS)6-hFc(IgG1) | 9.9/n.d. | 2.2./n.d | n.d | n.d |
| F8-500-C2 linked-(GGGS)6-mFc(IgG2A) | 15.0/n.d. | 3.5/n.d | n.d./1.1 | n.d/4 |
| F8-500-albumin | 7.8/9.1 | 1.7/1.1 | n.d. | n.d. |
| F8-500-albumin-His | 6.7/6.0 | ?/? | 1.6/0.6 | 16/6 |
| F8-500-albumin-Δa3 | 1.4/n.d. | 4.7/n.d. | n.d. | n.d. |
| 40K-PEG-O-F8-500-albumin-Δa3 | 12.0/n.d | 40/n.d. | n.d. | n.d. |
| F8-500-C2 linked-(GGGS)6-albumin | n.d/9.6 | n.d./1.1 | n.d. | n.d |
| F8-500-C2 linked-GS-albumin | 8.0/n.d. | 1.8./n.d | n.d./0.8 | n.d/3 |
| F8-500-hFcγRI | 9.2/9.7 | 2.0/1.1 | n.d. | n.d. |
| F8-500-hFcγRI-His | 10/n.d. | 2.2/n.d. | 1.7/1.2 | 17/12 |
| F8-500-hFcγRI-Δa3 | 0.2/n.d. | 0.7/n.d. | n.d. | n.d |
| F8-500-LRP-CR5-6 | 6.2/6.4 | 1.4/0.7 | n.d. | n.d |
| F8-500-ABD035-His | 10.3/— | ?/? | n.d./0.8 | n.d/8 |
| F8-GHBP-His | n.d | n.d. | 0.1/0.2 | 1/2 |
| F8-500-FIX47-125-His | 5.3/5.3 | ?/? | n.d. | n.d. |
| F8-500-F10AP-His | n.d | n.d. | 1.0/0.8 | 10/8 |

*Chromogenic assay/ELISA

The invention claimed is:

1. A fusion protein comprising a Factor VIII (FVIII) molecule and a fusion partner, wherein: (1) the FVIII molecule comprises a heavy chain and a light chain; and (2) the fusion partner is an Fcγ receptor or an immunoglobulin-binding fragment thereof fused to the N-terminus end of the light chain.

2. The fusion protein according to claim 1, wherein said Fcγ receptor is FcγRI comprising the amino acid sequence of SEQ ID NO:9.

3. The fusion protein of claim 1, wherein the FVIII molecule contains an amino acid substitution selected from the group consisting of Y1680F, Y1680R, Y1680N, E1682T and Y1680C numbered relative to SEQ ID NO: 1.

4. A pharmaceutical composition comprising a fusion protein according to claim 1.

5. A fusion protein comprising a B-domain truncated Factor VIII (FVIII) molecule and a fusion partner, wherein: (1) the FVIII molecule comprises a heavy chain and a light chain; (2) the fusion partner is an Fcγ receptor or an immunoglobulin-binding fragment thereof fused to the N-terminus end of the light chain; and (3) wherein residues 1649-1689 of the FVIII molecule numbered relative to SEQ ID NO:1 are fully or partially deleted.

6. A fusion protein comprising a B-domain truncated Factor VIII (FVIII) molecule and a fusion partner, wherein: (1) the FVIII molecule comprises a heavy chain and a light chain; (2) the fusion partner is an Fcγ receptor or an immunoglobulin-binding fragment thereof fused to the N-terminus end of the light chain; and (3) wherein residues 1647-1687 of the FVIII molecule numbered relative to SEQ ID NO:1 are fully or partially deleted.

7. A fusion protein comprising a B-domain truncated Factor VIII (FVIII) molecule and a fusion partner, wherein: (1) the FVIII molecule comprises a heavy chain and a light chain; (2) the fusion partner is an Fcγ receptor or an immunoglobulin-binding fragment thereof fused to the N-terminus end of the light chain; and (3) the heavy chain of the FVIII molecule comprises a truncated B-domain having the amino acid sequence of SEQ ID NO:2.

8. The fusion protein of claim 7, wherein the truncated B-domain has an O-linked glycan attached to Serine at residue 750 numbered relative to SEQ ID NO:1.

9. The fusion protein of claim 8, wherein a side group is attached to the O-linked glycan via a sialic acid.

10. The fusion protein of claim 9, wherein the side group is polyethylene glycol (PEG).

11. The fusion protein according to claim 7, wherein said Fcγ receptor is FcγRI comprising the amino acid sequence of SEQ ID NO:9.

12. The fusion protein of claim 7, wherein the FVIII molecule contains an amino acid substitution selected from the group consisting of Y1680F, Y1680R, Y1680N, E1682T and Y1680C numbered relative to SEQ ID NO:1.

13. A pharmaceutical composition comprising a fusion protein according to claim 7.

14. A fusion protein comprising a Factor VIII (FVIII) molecule and a fusion partner, wherein the Factor VIII molecule comprises a heavy chain and a light chain; the fusion partner is an Fcγ receptor or an immunoglobulin-binding fragment thereof fused to C-terminus end of the light chain.

15. A fusion protein comprising a B-domain truncated Factor VIII (FVIII) molecule and a fusion partner, wherein the Factor VIII molecule comprises a heavy chain and a light chain; the fusion partner is an Fcγ receptor or an immunoglobulin-binding fragment thereof fused to C-terminus end of the light chain.

16. The fusion protein of claim 15, wherein the truncated B-domain has an O-linked glycan attached to Serine at residue 750 numbered relative to SEQ ID NO:1.

17. The fusion protein of claim 16, wherein a side group is attached to the O-linked glycan via a sialic acid.

18. The fusion protein of claim 17, wherein the side group is polyethylene glycol (PEG).

19. A method for treating haemophilia comprising administering an effective amount of the molecule of claim 1 to a subject in need thereof.

* * * * *

SEQUENCE LISTING

<160> NUMBER OF SEQ ID NOS: 31

<210> SEQ ID NO 1
<211> LENGTH: 2332
<212> TYPE: PRT
<213> ORGANISM: homo sapiens

<400> SEQUENCE: 1

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

-continued

```
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
    115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
                180                 185                 190
His Lys Phe Ile Leu Leu Phe Ala Val Phe Asp Glu Gly Lys Ser Trp
            195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
```

```
                515                 520                 525
Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
930                 935                 940
```

```
Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335
```

-continued

Gln Trp Ser Lys Asn Met Lys His Leu Thr Pro Ser Thr Leu Thr
1340            1345                1350

Gln Ile Asp Tyr Asn Glu Lys Glu Lys Gly Ala Ile Thr Gln Ser
1355            1360                1365

Pro Leu Ser Asp Cys Leu Thr Arg Ser His Ser Ile Pro Gln Ala
1370            1375                1380

Asn Arg Ser Pro Leu Pro Ile Ala Lys Val Ser Ser Phe Pro Ser
1385            1390                1395

Ile Arg Pro Ile Tyr Leu Thr Arg Val Leu Phe Gln Asp Asn Ser
1400            1405                1410

Ser His Leu Pro Ala Ala Ser Tyr Arg Lys Lys Asp Ser Gly Val
1415            1420                1425

Gln Glu Ser Ser His Phe Leu Gln Gly Ala Lys Lys Asn Asn Leu
1430            1435                1440

Ser Leu Ala Ile Leu Thr Leu Glu Met Thr Gly Asp Gln Arg Glu
1445            1450                1455

Val Gly Ser Leu Gly Thr Ser Ala Thr Asn Ser Val Thr Tyr Lys
1460            1465                1470

Lys Val Glu Asn Thr Val Leu Pro Lys Pro Asp Leu Pro Lys Thr
1475            1480                1485

Ser Gly Lys Val Glu Leu Leu Pro Lys Val His Ile Tyr Gln Lys
1490            1495                1500

Asp Leu Phe Pro Thr Glu Thr Ser Asn Gly Ser Pro Gly His Leu
1505            1510                1515

Asp Leu Val Glu Gly Ser Leu Leu Gln Gly Thr Glu Gly Ala Ile
1520            1525                1530

Lys Trp Asn Glu Ala Asn Arg Pro Gly Lys Val Pro Phe Leu Arg
1535            1540                1545

Val Ala Thr Glu Ser Ser Ala Lys Thr Pro Ser Lys Leu Leu Asp
1550            1555                1560

Pro Leu Ala Trp Asp Asn His Tyr Gly Thr Gln Ile Pro Lys Glu
1565            1570                1575

Glu Trp Lys Ser Gln Glu Lys Ser Pro Glu Lys Thr Ala Phe Lys
1580            1585                1590

Lys Lys Asp Thr Ile Leu Ser Leu Asn Ala Cys Glu Ser Asn His
1595            1600                1605

Ala Ile Ala Ala Ile Asn Glu Gly Gln Asn Lys Pro Glu Ile Glu
1610            1615                1620

Val Thr Trp Ala Lys Gln Gly Arg Thr Glu Arg Leu Cys Ser Gln
1625            1630                1635

Asn Pro Pro Val Leu Lys Arg His Gln Arg Glu Ile Thr Arg Thr
1640            1645                1650

Thr Leu Gln Ser Asp Gln Glu Glu Ile Asp Tyr Asp Asp Thr Ile
1655            1660                1665

Ser Val Glu Met Lys Lys Glu Asp Phe Asp Ile Tyr Asp Glu Asp
1670            1675                1680

Glu Asn Gln Ser Pro Arg Ser Phe Gln Lys Lys Thr Arg His Tyr
1685            1690                1695

Phe Ile Ala Ala Val Glu Arg Leu Trp Asp Tyr Gly Met Ser Ser
1700            1705                1710

Ser Pro His Val Leu Arg Asn Arg Ala Gln Ser Gly Ser Val Pro
1715            1720                1725

Gln Phe Lys Lys Val Val Phe Gln Glu Phe Thr Asp Gly Ser Phe

-continued

```
            1730                1735                1740

Thr Gln Pro Leu Tyr Arg Gly Glu Leu Asn Glu His Leu Gly Leu
            1745                1750                1755

Leu Gly Pro Tyr Ile Arg Ala Glu Val Glu Asp Asn Ile Met Val
            1760                1765                1770

Thr Phe Arg Asn Gln Ala Ser Arg Pro Tyr Ser Phe Tyr Ser Ser
            1775                1780                1785

Leu Ile Ser Tyr Glu Glu Asp Gln Arg Gln Gly Ala Glu Pro Arg
            1790                1795                1800

Lys Asn Phe Val Lys Pro Asn Glu Thr Lys Thr Tyr Phe Trp Lys
            1805                1810                1815

Val Gln His His Met Ala Pro Thr Lys Asp Glu Phe Asp Cys Lys
            1820                1825                1830

Ala Trp Ala Tyr Phe Ser Asp Val Asp Leu Glu Lys Asp Val His
            1835                1840                1845

Ser Gly Leu Ile Gly Pro Leu Leu Val Cys His Thr Asn Thr Leu
            1850                1855                1860

Asn Pro Ala His Gly Arg Gln Val Thr Val Gln Glu Phe Ala Leu
            1865                1870                1875

Phe Phe Thr Ile Phe Asp Glu Thr Lys Ser Trp Tyr Phe Thr Glu
            1880                1885                1890

Asn Met Glu Arg Asn Cys Arg Ala Pro Cys Asn Ile Gln Met Glu
            1895                1900                1905

Asp Pro Thr Phe Lys Glu Asn Tyr Arg Phe His Ala Ile Asn Gly
            1910                1915                1920

Tyr Ile Met Asp Thr Leu Pro Gly Leu Val Met Ala Gln Asp Gln
            1925                1930                1935

Arg Ile Arg Trp Tyr Leu Leu Ser Met Gly Ser Asn Glu Asn Ile
            1940                1945                1950

His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe
            1970                1975                1980

Glu Thr Val Glu Met Leu Pro Ser Lys Ala Gly Ile Trp Arg Val
            1985                1990                1995

Glu Cys Leu Ile Gly Glu His Leu His Ala Gly Met Ser Thr Leu
            2000                2005                2010

Phe Leu Val Tyr Ser Asn Lys Cys Gln Thr Pro Leu Gly Met Ala
            2015                2020                2025

Ser Gly His Ile Arg Asp Phe Gln Ile Thr Ala Ser Gly Gln Tyr
            2030                2035                2040

Gly Gln Trp Ala Pro Lys Leu Ala Arg Leu His Tyr Ser Gly Ser
            2045                2050                2055

Ile Asn Ala Trp Ser Thr Lys Glu Pro Phe Ser Trp Ile Lys Val
            2060                2065                2070

Asp Leu Leu Ala Pro Met Ile Ile His Gly Ile Lys Thr Gln Gly
            2075                2080                2085

Ala Arg Gln Lys Phe Ser Ser Leu Tyr Ile Ser Gln Phe Ile Ile
            2090                2095                2100

Met Tyr Ser Leu Asp Gly Lys Lys Trp Gln Thr Tyr Arg Gly Asn
            2105                2110                2115

Ser Thr Gly Thr Leu Met Val Phe Phe Gly Asn Val Asp Ser Ser
            2120                2125                2130
```

-continued

```
Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 2
<211> LENGTH: 21
<212> TYPE: PRT
<213> ORGANISM: artificial
<220> FEATURE:
<223> OTHER INFORMATION: FVIII B domain linker of 21 amino acids

<400> SEQUENCE: 2

Ser Phe Ser Gln Asn Ser Arg His Pro Ser Gln Asn Pro Pro Val Leu
1               5                   10                  15

Lys Arg His Gln Arg
            20

<210> SEQ ID NO 3
<211> LENGTH: 28
<212> TYPE: PRT
<213> ORGANISM: artificial
<220> FEATURE:
<223> OTHER INFORMATION: F8-500-His linker

<400> SEQUENCE: 3

Ser Phe Ser Gln Asn Ser Arg His Pro Ser His His His His His His
1               5                   10                  15

Ser Gln Asn Pro Pro Val Leu Lys Arg His Gln Arg
            20                  25

<210> SEQ ID NO 4
<211> LENGTH: 28
<212> TYPE: PRT
```

<213> ORGANISM: artificial
<220> FEATURE:
<223> OTHER INFORMATION: F8-500-alpha a3 His linker

<400> SEQUENCE: 4

Ser Phe Ser Gln Asn Ser Arg His Pro Ser His His His His His
1               5                   10                  15

Ser Gln Asn Pro Pro Val Leu Lys Arg His Gln Arg
            20                  25

<210> SEQ ID NO 5
<211> LENGTH: 224
<212> TYPE: PRT
<213> ORGANISM: artificial
<220> FEATURE:
<223> OTHER INFORMATION: hFc

<400> SEQUENCE: 5

His Thr Cys Pro Pro Cys Pro Ala Pro Glu Ala Glu Gly Glu Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Gln Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Asp Glu Leu Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 6
<211> LENGTH: 226
<212> TYPE: PRT
<213> ORGANISM: artificial
<220> FEATURE:
<223> OTHER INFORMATION: mFc

<400> SEQUENCE: 6

Lys Pro Cys Pro Pro Cys Lys Cys Pro Ala Pro Asn Ala Glu Gly Glu
1               5                   10                  15

Pro Ser Val Phe Ile Phe Pro Pro Lys Ile Lys Asp Val Leu Met Ile
            20                  25                  30

```
Ser Leu Ser Pro Met Val Thr Cys Val Val Asp Val Ser Glu Asp
        35                  40                  45

Asp Pro Asp Val Gln Ile Ser Trp Phe Val Asn Asn Val Glu Val Leu
50                  55                  60

Thr Ala Gln Thr Gln Thr His Arg Glu Asp Tyr Gln Ser Thr Leu Arg
65                  70                  75                  80

Val Val Ser Ala Leu Pro Ile Gln His Gln Asp Trp Met Ser Gly Lys
                85                  90                  95

Glu Phe Lys Cys Lys Val Asn Asn Lys Ala Leu Pro Ala Pro Ile Glu
            100                 105                 110

Arg Thr Ile Ser Lys Pro Lys Gly Ser Val Arg Ala Pro Gln Val Tyr
        115                 120                 125

Val Leu Pro Pro Pro Glu Glu Glu Met Thr Lys Lys Gln Val Thr Leu
130                 135                 140

Thr Cys Met Val Thr Asp Phe Met Pro Glu Asp Ile Tyr Val Glu Trp
145                 150                 155                 160

Thr Asn Asn Gly Lys Thr Glu Leu Asn Tyr Lys Asn Thr Glu Pro Val
                165                 170                 175

Leu Asp Ser Asp Gly Ser Tyr Phe Met Tyr Ser Lys Leu Arg Val Glu
            180                 185                 190

Lys Lys Asn Trp Val Glu Arg Asn Ser Tyr Ser Cys Ser Val Val His
        195                 200                 205

Glu Gly Leu His Asn His His Thr Thr Lys Ser Phe Ser Arg Thr Pro
210                 215                 220

Gly Lys
225

<210> SEQ ID NO 7
<211> LENGTH: 585
<212> TYPE: PRT
<213> ORGANISM: homo sapiens

<400> SEQUENCE: 7

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
```

-continued

```
                165                 170                 175
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 8
<211> LENGTH: 678
<212> TYPE: PRT
<213> ORGANISM: homo sapiens

<400> SEQUENCE: 8

```
Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
            20                  25                  30

Asp Gly Pro Ser Val Ala Cys Val Lys Lys Ala Ser Tyr Leu Asp Cys
        35                  40                  45

Ile Arg Ala Ile Ala Ala Asn Glu Ala Asp Ala Val Thr Leu Asp Ala
    50                  55                  60

Gly Leu Val Tyr Asp Ala Tyr Leu Ala Pro Asn Asn Leu Lys Pro Val
65                  70                  75                  80

Val Ala Glu Phe Tyr Gly Ser Lys Glu Asp Pro Gln Thr Phe Tyr Ala
                85                  90                  95

Val Ala Val Val Lys Lys Asp Ser Gly Phe Gln Met Asn Gln Leu Arg
            100                 105                 110

Gly Lys Lys Ser Cys His Thr Gly Leu Gly Arg Ser Ala Gly Trp Asn
        115                 120                 125

Ile Pro Ile Gly Leu Leu Tyr Cys Asp Leu Pro Glu Pro Arg Lys Pro
    130                 135                 140

Leu Glu Lys Ala Val Ala Asn Phe Phe Ser Gly Ser Cys Ala Pro Cys
145                 150                 155                 160

Ala Asp Gly Thr Asp Phe Pro Gln Leu Cys Gln Leu Cys Pro Gly Cys
                165                 170                 175

Gly Cys Ser Thr Leu Asn Gln Tyr Phe Gly Tyr Ser Gly Ala Phe Lys
            180                 185                 190

Cys Leu Lys Asp Gly Ala Gly Asp Val Ala Phe Val Lys His Ser Thr
        195                 200                 205

Ile Phe Glu Asn Leu Ala Asn Lys Ala Asp Arg Asp Gln Tyr Glu Leu
    210                 215                 220

Leu Cys Leu Asp Asn Thr Arg Lys Pro Val Asp Glu Tyr Lys Asp Cys
225                 230                 235                 240

His Leu Ala Gln Val Pro Ser His Thr Val Val Ala Arg Ser Met Gly
                245                 250                 255

Gly Lys Glu Asp Leu Ile Trp Glu Leu Leu Asn Gln Ala Gln Glu His
            260                 265                 270

Phe Gly Lys Asp Lys Ser Lys Glu Phe Gln Leu Phe Ser Ser Pro His
        275                 280                 285

Gly Lys Asp Leu Leu Phe Lys Asp Ser Ala His Gly Phe Leu Lys Val
    290                 295                 300

Pro Pro Arg Met Asp Ala Lys Met Tyr Leu Gly Tyr Glu Tyr Val Thr
305                 310                 315                 320

Ala Ile Arg Asn Leu Arg Glu Gly Thr Cys Pro Glu Ala Pro Thr Asp
                325                 330                 335

Glu Cys Lys Pro Val Lys Trp Cys Ala Leu Ser His His Glu Arg Leu
            340                 345                 350

Lys Cys Asp Glu Trp Ser Val Asn Ser Val Gly Lys Ile Glu Cys Val
        355                 360                 365

Ser Ala Glu Thr Thr Glu Asp Cys Ile Ala Lys Ile Met Asn Gly Glu
```

```
                    370                 375                 380
Ala Asp Ala Met Ser Leu Asp Gly Gly Phe Val Tyr Ile Ala Gly Lys
385                 390                 395                 400

Cys Gly Leu Val Pro Val Leu Ala Glu Asn Tyr Asn Lys Ser Asp Asn
                405                 410                 415

Cys Glu Asp Thr Pro Glu Ala Gly Tyr Phe Ala Val Ala Val Val Lys
            420                 425                 430

Lys Ser Ala Ser Asp Leu Thr Trp Asp Asn Leu Lys Gly Lys Lys Ser
        435                 440                 445

Cys His Thr Ala Val Gly Arg Thr Ala Gly Trp Asn Ile Pro Met Gly
    450                 455                 460

Leu Leu Tyr Asn Lys Ile Asn His Cys Arg Phe Asp Glu Phe Phe Ser
465                 470                 475                 480

Glu Gly Cys Ala Pro Gly Ser Lys Lys Asp Ser Ser Leu Cys Lys Leu
                485                 490                 495

Cys Met Gly Ser Gly Leu Asn Leu Cys Glu Pro Asn Asn Lys Glu Gly
            500                 505                 510

Tyr Tyr Gly Tyr Thr Gly Ala Phe Arg Cys Leu Val Glu Lys Gly Asp
        515                 520                 525

Val Ala Phe Val Lys His Gln Thr Val Pro Gln Asn Thr Gly Gly Lys
    530                 535                 540

Asn Pro Asp Pro Trp Ala Lys Asn Leu Asn Glu Lys Asp Tyr Glu Leu
545                 550                 555                 560

Leu Cys Leu Asp Gly Thr Arg Lys Pro Val Glu Glu Tyr Ala Asn Cys
                565                 570                 575

His Leu Ala Arg Ala Pro Asn His Ala Val Val Thr Arg Lys Asp Lys
            580                 585                 590

Glu Ala Cys Val His Lys Ile Leu Arg Gln Gln His Leu Phe Gly
        595                 600                 605

Ser Asn Val Thr Asp Cys Ser Gly Asn Phe Cys Leu Phe Arg Ser Glu
    610                 615                 620

Thr Lys Asp Leu Leu Phe Arg Asp Asp Thr Val Cys Leu Ala Lys Leu
625                 630                 635                 640

His Asp Arg Asn Thr Tyr Glu Lys Tyr Leu Gly Glu Glu Tyr Val Lys
                645                 650                 655

Ala Val Gly Asn Leu Arg Lys Cys Ser Thr Ser Ser Leu Leu Glu Ala
            660                 665                 670

Cys Thr Phe Arg Arg Pro
        675

<210> SEQ ID NO 9
<211> LENGTH: 273
<212> TYPE: PRT
<213> ORGANISM: homo sapiens

<400> SEQUENCE: 9

Gln Val Asp Thr Thr Lys Ala Val Ile Thr Leu Gln Pro Pro Trp Val
1               5                   10                  15

Ser Val Phe Gln Glu Glu Thr Val Thr Leu His Cys Glu Val Leu His
            20                  25                  30

Leu Pro Gly Ser Ser Ser Thr Gln Trp Phe Leu Asn Gly Thr Ala Thr
        35                  40                  45

Gln Thr Ser Thr Pro Ser Tyr Arg Ile Thr Ser Ala Ser Val Asn Asp
    50                  55                  60
```

```
Ser Gly Glu Tyr Arg Cys Gln Arg Gly Leu Ser Gly Arg Ser Asp Pro
 65                  70                  75                  80

Ile Gln Leu Glu Ile His Arg Gly Trp Leu Leu Gln Val Ser Ser
                 85                  90                  95

Arg Val Phe Thr Glu Gly Glu Pro Leu Ala Leu Arg Cys His Ala Trp
            100                 105                 110

Lys Asp Lys Leu Val Tyr Asn Val Leu Tyr Tyr Arg Asn Gly Lys Ala
        115                 120                 125

Phe Lys Phe Phe His Trp Asn Ser Asn Leu Thr Ile Leu Lys Thr Asn
    130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
            180                 185                 190

Val Thr Leu Ser Cys Glu Thr Lys Leu Leu Leu Gln Arg Pro Gly Leu
        195                 200                 205

Gln Leu Tyr Phe Ser Phe Tyr Met Gly Ser Lys Thr Leu Arg Gly Arg
    210                 215                 220

Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
            260                 265                 270

Pro

<210> SEQ ID NO 10
<211> LENGTH: 274
<212> TYPE: PRT
<213> ORGANISM: homo sapiens

<400> SEQUENCE: 10

Ala Glu Ser His Leu Ser Leu Leu Tyr His Leu Thr Ala Val Ser Ser
  1               5                  10                  15

Pro Ala Pro Gly Thr Pro Ala Phe Trp Val Ser Gly Trp Leu Gly Pro
             20                  25                  30

Gln Gln Tyr Leu Ser Tyr Asn Ser Leu Arg Gly Glu Ala Glu Pro Cys
         35                  40                  45

Gly Ala Trp Val Trp Glu Asn Gln Val Ser Trp Tyr Trp Glu Lys Glu
     50                  55                  60

Thr Thr Asp Leu Arg Ile Lys Glu Lys Leu Phe Leu Glu Ala Phe Lys
 65                  70                  75                  80

Ala Leu Gly Gly Lys Gly Pro Tyr Thr Leu Gln Gly Leu Leu Gly Cys
                 85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160
```

His Arg Leu Arg Glu His Leu Glu Arg Gly Arg Gly Asn Leu Glu Trp
            165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
            195                 200                 205

Gln Leu Arg Phe Leu Arg Asn Gly Leu Ala Ala Gly Thr Gly Gln Gly
            210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
            245                 250                 255

Ala Gly Leu Ala Gln Pro Leu Arg Val Glu Leu Glu Ser Pro Ala Lys
            260                 265                 270

Ser Ser

<210> SEQ ID NO 11
<211> LENGTH: 274
<212> TYPE: PRT
<213> ORGANISM: artificial
<220> FEATURE:
<223> OTHER INFORMATION: FcRn-H166K

<400> SEQUENCE: 11

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
            35                  40                  45

Gly Ala Trp Val Trp Glu Asn Gln Val Ser Trp Tyr Trp Glu Lys Glu
        50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
            85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
            115                 120                 125

Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu Lys Leu Glu Arg Gly Arg Gly Asn Leu Glu Trp
            165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
            195                 200                 205

Gln Leu Arg Phe Leu Arg Asn Gly Leu Ala Ala Gly Thr Gly Gln Gly
            210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His

```
                245                 250                 255
Ala Gly Leu Ala Gln Pro Leu Arg Val Glu Leu Glu Ser Pro Ala Lys
            260                 265                 270
Ser Ser
```

<210> SEQ ID NO 12
<211> LENGTH: 79
<212> TYPE: PRT
<213> ORGANISM: artificial
<220> FEATURE:
<223> OTHER INFORMATION: LRP-CR5-6

<400> SEQUENCE: 12

```
Thr Cys Pro Pro Asn Gln Phe Ser Cys Ala Ser Gly Arg Cys Ile Pro
  1               5                  10                  15
Ile Ser Trp Thr Cys Asp Leu Asp Asp Cys Gly Asp Arg Ser Asp
            20                  25                  30
Glu Ser Ala Ser Cys Ala Tyr Pro Thr Cys Phe Pro Leu Thr Gln Phe
        35                  40                  45
Thr Cys Asn Asn Gly Arg Cys Ile Asn Ile Trp Arg Cys Asp Asn
    50                  55                  60
Asp Asn Asp Cys Gly Asp Asn Ser Asp Glu Ala Gly Cys Ser His
65                  70                  75
```

<210> SEQ ID NO 13
<211> LENGTH: 83
<212> TYPE: PRT
<213> ORGANISM: artificial
<220> FEATURE:
<223> OTHER INFORMATION: LRP-CR6-7

<400> SEQUENCE: 13

```
Thr Cys Phe Pro Leu Thr Gln Phe Thr Cys Asn Asn Gly Arg Cys Ile
  1               5                  10                  15
Asn Ile Asn Trp Arg Cys Asp Asn Asp Asn Asp Cys Gly Asp Asn Ser
                20                  25                  30
Asp Glu Ala Gly Cys Ser His Ser Cys Ser Ser Thr Gln Phe Lys Cys
            35                  40                  45
Asn Ser Gly Arg Cys Ile Pro Glu His Trp Thr Cys Asp Gly Asp Asn
    50                  55                  60
Asp Cys Gly Asp Tyr Ser Asp Glu Thr His Ala Asn Cys Thr Asn Gln
65                  70                  75                  80
Ala Thr Arg
```

<210> SEQ ID NO 14
<211> LENGTH: 39
<212> TYPE: PRT
<213> ORGANISM: artificial
<220> FEATURE:
<223> OTHER INFORMATION: LRP-CR6

<400> SEQUENCE: 14

```
Thr Cys Phe Pro Leu Thr Gln Phe Thr Cys Asn Asn Gly Arg Cys Ile
  1               5                  10                  15
Asn Ile Asn Trp Arg Cys Asp Asn Asp Asn Asp Cys Gly Asp Asn Ser
                20                  25                  30
Asp Glu Ala Gly Cys Ser His
            35
```

<210> SEQ ID NO 15
<211> LENGTH: 243
<212> TYPE: PRT
<213> ORGANISM: artificial
<220> FEATURE:
<223> OTHER INFORMATION: SC anti-GPIIIa-1-HC-LC

<400> SEQUENCE: 15

Met Asp Ile Leu Met Thr Gln Ser Pro Ser Ser Met Ser Val Ser Leu
1               5                   10                  15

Gly Asp Thr Val Ser Ile Thr Cys His Ala Ser Gln Gly Ile Ser Ser
            20                  25                  30

Asn Ile Gly Trp Leu Gln Gln Lys Pro Gly Lys Ser Phe Met Gly Leu
        35                  40                  45

Ile Tyr Tyr Gly Thr Asn Leu Val Asp Gly Val Pro Ser Arg Phe Ser
    50                  55                  60

Gly Ser Gly Ser Gly Ala Asp Tyr Ser Leu Thr Ile Ser Ser Leu Asp
65                  70                  75                  80

Ser Glu Asp Phe Ala Asp Tyr Tyr Cys Val Gln Tyr Ala Gln Leu Pro
                85                  90                  95

Tyr Thr Phe Gly Gly Gly Thr Lys Leu Glu Lys Leu Gly Gly Gly Gly
            100                 105                 110

Ser Gly Gly Gly Gly Ser Gly Gly Gly Ser Asn Ser Val Gln Leu
        115                 120                 125

Gln Gln Ser Gly Ala Glu Leu Val Lys Pro Gly Ala Ser Val Lys Leu
    130                 135                 140

Ser Cys Thr Ala Ser Gly Phe Asn Ile Lys Asp Thr Tyr Val His Trp
145                 150                 155                 160

Val Lys Gln Arg Pro Glu Gln Gly Leu Glu Trp Ile Gly Arg Ile Asp
                165                 170                 175

Pro Ala Asn Gly Tyr Thr Lys Tyr Asp Pro Lys Phe Gln Gly Lys Ala
            180                 185                 190

Thr Ile Thr Ala Asp Thr Ser Ser Asn Thr Ala Tyr Leu Gln Leu Ser
        195                 200                 205

Ser Leu Thr Ser Glu Asp Thr Ala Val Tyr Tyr Cys Val Arg Pro Leu
    210                 215                 220

Tyr Asp Tyr Tyr Ala Met Asp Tyr Trp Gly Gln Gly Thr Ser Val Thr
225                 230                 235                 240

Val Ser Ser

<210> SEQ ID NO 16
<211> LENGTH: 258
<212> TYPE: PRT
<213> ORGANISM: artificial
<220> FEATURE:
<223> OTHER INFORMATION: Linker-SC anti-GPIIIa-1-HC-LC

<400> SEQUENCE: 16

Met Asp Ile Leu Met Thr Gln Ser Pro Ser Ser Met Ser Val Ser Leu
1               5                   10                  15

Gly Asp Thr Val Ser Ile Thr Cys His Ala Ser Gln Gly Ile Ser Ser
            20                  25                  30

Asn Ile Gly Trp Leu Gln Gln Lys Pro Gly Lys Ser Phe Met Gly Leu
        35                  40                  45

Ile Tyr Tyr Gly Thr Asn Leu Val Asp Gly Val Pro Ser Arg Phe Ser
    50                  55                  60

Gly Ser Gly Ser Gly Ala Asp Tyr Ser Leu Thr Ile Ser Ser Leu Asp

```
                65                  70                  75                  80
Ser Glu Asp Phe Ala Asp Tyr Tyr Cys Val Gln Tyr Ala Gln Leu Pro
                    85                  90                  95
Tyr Thr Phe Gly Gly Gly Thr Lys Leu Glu Lys Leu Gly Gly Gly Gly
                100                 105                 110
Ser Gly Gly Gly Gly Ser Gly Gly Gly Ser Asn Ser Val Gln Leu
            115                 120                 125
Gln Gln Ser Gly Ala Glu Leu Val Lys Pro Gly Ala Ser Val Lys Leu
        130                 135                 140
Ser Cys Thr Ala Ser Gly Phe Asn Ile Lys Asp Thr Tyr Val His Trp
145                 150                 155                 160
Val Lys Gln Arg Pro Glu Gln Gly Leu Glu Trp Ile Gly Arg Ile Asp
                165                 170                 175
Pro Ala Asn Gly Tyr Thr Lys Tyr Asp Pro Lys Phe Gln Gly Lys Ala
            180                 185                 190
Thr Ile Thr Ala Asp Thr Ser Ser Asn Thr Ala Tyr Leu Gln Leu Ser
        195                 200                 205
Ser Leu Thr Ser Glu Asp Thr Ala Val Tyr Tyr Cys Val Arg Pro Leu
    210                 215                 220
Tyr Asp Tyr Tyr Ala Met Asp Tyr Trp Gly Gln Gly Thr Ser Val Thr
225                 230                 235                 240
Val Ser Ser Gly Gly Gly Gly Ser Gly Gly Gly Gly Ser Gly Gly Gly
                245                 250                 255
Gly Ser

<210> SEQ ID NO 17
<211> LENGTH: 248
<212> TYPE: PRT
<213> ORGANISM: artificial
<220> FEATURE:
<223> OTHER INFORMATION: SC anti-GPIIIa-2-HC-LC

<400> SEQUENCE: 17

Gln Val Gln Leu Gln Gln Ser Gly Ala Glu Leu Val Arg Pro Gly Thr
1               5                   10                  15
Ser Val Lys Ile Ser Cys Lys Ala Ser Gly Tyr Thr Phe Thr Asn Tyr
                20                  25                  30
Trp Leu Gly Trp Val Lys Gln Arg Pro Gly His Gly Leu Glu Trp Ile
            35                  40                  45
Gly Asp Ile Tyr Pro Gly Gly Gly Tyr Asn Lys Tyr Asn Glu Asn Phe
        50                  55                  60
Lys Gly Lys Ala Thr Leu Thr Ala Asp Thr Ser Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Glu Tyr Gly Asn Tyr Asp Tyr Ala Met Asp Ser Trp Gly Gln
                100                 105                 110
Gly Thr Ser Val Thr Val Ser Ser Gly Gly Gly Gly Ser Gly Gly Gly
            115                 120                 125
Gly Ser Gly Gly Gly Gly Ser Asp Ile Val Met Thr Gln Ala Ala Pro
        130                 135                 140
Ser Val Pro Val Thr Pro Gly Glu Ser Val Ser Ile Ser Cys Arg Ser
145                 150                 155                 160
Ser Arg Ser Leu Leu His Ser Asn Gly Asn Thr Tyr Leu Cys Trp Phe
                165                 170                 175
```

```
Leu Gln Arg Pro Gly Gln Ser Pro Gln Leu Leu Ile Tyr Arg Met Ser
            180                 185                 190

Asn Leu Ala Ser Gly Val Pro Asp Arg Phe Ser Gly Ser Gly Ser Gly
            195                 200                 205

Thr Ala Phe Thr Leu Arg Ile Ser Arg Val Glu Ala Glu Asp Val Gly
            210                 215                 220

Val Tyr Tyr Cys Met Gln His Leu Glu Tyr Pro Phe Thr Phe Gly Ser
225                 230                 235                 240

Gly Thr Lys Leu Glu Ile Lys Arg
                245

<210> SEQ ID NO 18
<211> LENGTH: 248
<212> TYPE: PRT
<213> ORGANISM: artificial
<220> FEATURE:
<223> OTHER INFORMATION: SC anti-GPIIIa-2-LC-HC

<400> SEQUENCE: 18

Asp Ile Val Met Thr Gln Ala Ala Pro Ser Val Pro Val Thr Pro Gly
1               5                   10                  15

Glu Ser Val Ser Ile Ser Cys Arg Ser Arg Ser Leu Leu His Ser
            20                  25                  30

Asn Gly Asn Thr Tyr Leu Cys Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Gly Gly Gly Gly Ser Gly Gly Gly Ser Gly Gly Gly Gly Ser
            115                 120                 125

Gln Val Gln Leu Gln Gln Ser Gly Ala Glu Leu Val Arg Pro Gly Thr
        130                 135                 140

Ser Val Lys Ile Ser Cys Lys Ala Ser Gly Tyr Thr Phe Thr Asn Tyr
145                 150                 155                 160

Trp Leu Gly Trp Val Lys Gln Arg Pro Gly His Gly Leu Glu Trp Ile
                165                 170                 175

Gly Asp Ile Tyr Pro Gly Gly Gly Tyr Asn Lys Tyr Asn Glu Asn Phe
            180                 185                 190

Lys Gly Lys Ala Thr Leu Thr Ala Asp Thr Ser Ser Thr Ala Tyr
            195                 200                 205

Met Gln Leu Ser Ser Leu Thr Ser Glu Asp Ser Ala Val Tyr Phe Cys
            210                 215                 220

Ala Arg Glu Tyr Gly Asn Tyr Asp Tyr Ala Met Asp Ser Trp Gly Gln
225                 230                 235                 240

Gly Thr Ser Val Thr Val Ser Ser
                245

<210> SEQ ID NO 19
<211> LENGTH: 46
<212> TYPE: PRT
<213> ORGANISM: artificial
```

<220> FEATURE:
<223> OTHER INFORMATION: ABD035

<400> SEQUENCE: 19

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
                20                  25                  30

Gly Val Glu Ala Leu Lys Leu His Ile Leu Ala Ala Leu Pro
            35                  40                  45

<210> SEQ ID NO 20
<211> LENGTH: 865
<212> TYPE: PRT
<213> ORGANISM: Artificial
<220> FEATURE:
<223> OTHER INFORMATION: Sequence A

<400> SEQUENCE: 20

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
                20                  25                  30

Gly Ser Ala Pro Gly Ser Pro Ala Gly Ser Pro Thr Ser Thr Glu Glu
            35                  40                  45

Gly Thr Ser Thr Glu Pro Ser Glu Gly Ser Ala Pro Gly Thr Ser Thr
            50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
                115                 120                 125

Glu Ser Gly Pro Gly Thr Ser Thr Glu Pro Ser Glu Gly Ser Ala Pro
            130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Glu Pro Ser Glu Gly Ser Ala Pro
                180                 185                 190

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Ser Glu Ser Ala Thr Pro
        210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
            275                 280                 285

Gly Ser Pro Ala Gly Ser Pro Thr Ser Thr Glu Glu Gly Thr Ser Glu

-continued

|     | 290 |     |     | 295 |     |     | 300 |     |     |     |     |
|-----|-----|-----|-----|-----|-----|-----|-----|-----|-----|-----|-----|

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
                340                 345                 350

Glu Pro Ser Glu Gly Ser Ala Pro Gly Thr Ser Thr Glu Pro Ser Glu
                355                 360                 365

Gly Ser Ala Pro Gly Thr Ser Thr Glu Pro Ser Glu Gly Ser Ala Pro
                370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
                420                 425                 430

Gly Thr Ser Glu Ser Ala Thr Pro Glu Ser Gly Pro Gly Ser Glu Pro
                435                 440                 445

Ala Thr Ser Gly Ser Glu Thr Pro Gly Thr Ser Glu Ser Ala Thr Pro
450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
                500                 505                 510

Glu Ser Gly Pro Gly Ser Pro Ala Gly Ser Pro Thr Ser Thr Glu Glu
                515                 520                 525

Gly Ser Pro Ala Gly Ser Pro Thr Ser Thr Glu Glu Gly Ser Pro Ala
                530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

Gly Thr Ser Glu Ser Ala Thr Pro Glu Ser Gly Pro Gly Ser Glu Pro
                580                 585                 590

Ala Thr Ser Gly Ser Glu Thr Pro Gly Thr Ser Glu Ser Ala Thr Pro
                595                 600                 605

Glu Ser Gly Pro Gly Ser Glu Pro Ala Thr Ser Gly Ser Glu Thr Pro
                610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
                645                 650                 655

Ser Thr Glu Glu Gly Thr Ser Glu Ser Ala Thr Pro Glu Ser Gly Pro
                660                 665                 670

Gly Ser Glu Pro Ala Thr Ser Gly Ser Glu Thr Pro Gly Thr Ser Glu
                675                 680                 685

Ser Ala Thr Pro Glu Ser Gly Pro Gly Ser Pro Ala Gly Ser Pro Thr
                690                 695                 700

Ser Thr Glu Glu Gly Ser Pro Ala Gly Ser Pro Thr Ser Thr Glu Glu
705                 710                 715                 720

-continued

```
Gly Thr Ser Thr Glu Pro Ser Glu Gly Ser Ala Pro Gly Thr Ser Glu
                725                 730                 735

Ser Ala Thr Pro Glu Ser Gly Pro Gly Thr Ser Glu Ser Ala Thr Pro
            740                 745                 750

Glu Ser Gly Pro Gly Thr Ser Glu Ser Ala Thr Pro Glu Ser Gly Pro
        755                 760                 765

Gly Ser Glu Pro Ala Thr Ser Gly Ser Glu Thr Pro Gly Ser Glu Pro
    770                 775                 780

Ala Thr Ser Gly Ser Glu Thr Pro Gly Ser Pro Ala Gly Ser Pro Thr
785                 790                 795                 800

Ser Thr Glu Glu Gly Thr Ser Thr Glu Pro Ser Glu Gly Ser Ala Pro
                805                 810                 815

Gly Thr Ser Thr Glu Pro Ser Glu Gly Ser Ala Pro Gly Ser Glu Pro
            820                 825                 830

Ala Thr Ser Gly Ser Glu Thr Pro Gly Thr Ser Glu Ser Ala Thr Pro
        835                 840                 845

Glu Ser Gly Pro Gly Thr Ser Thr Glu Pro Ser Glu Gly Ser Ala Pro
    850                 855                 860

Gly
865

<210> SEQ ID NO 21
<211> LENGTH: 400
<212> TYPE: PRT
<213> ORGANISM: artificial
<220> FEATURE:
<223> OTHER INFORMATION: ELP80

<400> SEQUENCE: 21

Gly Val Pro Gly Val Gly Val Pro Gly Gly Val Pro Gly Val Gly Val
1               5                   10                  15

Val Pro Gly Val Gly Val Pro Gly Ala Gly Val Pro Gly Val Gly Val
            20                  25                  30

Pro Gly Gly Gly Val Pro Gly Val Gly Val Pro Gly Val Gly Val Pro
        35                  40                  45

Gly Ala Gly Val Pro Gly Val Gly Val Pro Gly Gly Gly Val Pro Gly
    50                  55                  60

Val Gly Val Pro Gly Val Gly Val Pro Gly Ala Gly Val Pro Gly Val
65                  70                  75                  80

Gly Val Pro Gly Gly Gly Val Pro Gly Val Gly Val Pro Gly Val Gly
                85                  90                  95

Val Pro Gly Ala Gly Val Pro Gly Val Gly Val Pro Gly Gly Gly Val
            100                 105                 110

Pro Gly Val Gly Val Pro Gly Val Gly Val Pro Gly Ala Gly Val Pro
        115                 120                 125

Gly Val Gly Val Pro Gly Gly Gly Val Pro Gly Val Gly Val Pro Gly
    130                 135                 140

Val Gly Val Pro Gly Ala Gly Val Pro Gly Val Gly Val Pro Gly Gly
145                 150                 155                 160

Gly Val Pro Gly Val Gly Val Pro Gly Val Gly Val Pro Gly Ala Gly
                165                 170                 175

Val Pro Gly Val Gly Val Pro Gly Gly Gly Val Pro Gly Val Gly Val
            180                 185                 190

Pro Gly Val Gly Val Pro Gly Ala Gly Val Pro Gly Val Gly Val Pro
        195                 200                 205
```

```
Gly Gly Gly Val Pro Gly Val Gly Val Pro Gly Val Gly Val Pro Gly
        210                 215                 220
Ala Gly Val Pro Gly Val Gly Val Pro Gly Gly Gly Val Pro Gly Val
225                 230                 235                 240
Gly Val Pro Gly Val Gly Val Pro Gly Ala Gly Val Pro Gly Val Gly
                245                 250                 255
Val Pro Gly Gly Val Pro Gly Val Gly Val Pro Gly Val Gly Val
            260                 265                 270
Pro Gly Ala Gly Val Pro Gly Val Gly Val Pro Gly Gly Gly Val Pro
        275                 280                 285
Gly Val Gly Val Pro Gly Val Gly Val Pro Gly Ala Gly Val Pro Gly
        290                 295                 300
Val Gly Val Pro Gly Gly Gly Val Pro Gly Val Gly Val Pro Gly Val
305                 310                 315                 320
Gly Val Pro Gly Ala Gly Val Pro Gly Val Gly Val Pro Gly Gly Gly
                325                 330                 335
Val Pro Gly Val Gly Val Pro Gly Val Gly Val Pro Gly Ala Gly Val
            340                 345                 350
Pro Gly Val Gly Val Pro Gly Gly Val Pro Gly Val Gly Val Pro
        355                 360                 365
Gly Val Gly Val Pro Gly Ala Gly Val Pro Gly Val Gly Val Pro Gly
        370                 375                 380
Gly Gly Val Pro Gly Val Gly Val Pro Gly Val Gly Val Pro Gly Ala
385                 390                 395                 400

<210> SEQ ID NO 22
<211> LENGTH: 41
<212> TYPE: PRT
<213> ORGANISM: artificial
<220> FEATURE:
<223> OTHER INFORMATION: Extra a3

<400> SEQUENCE: 22

Glu Ile Thr Arg Thr Thr Leu Gln Ser Asp Gln Glu Glu Ile Asp Tyr
1               5                   10                  15
Asp Asp Thr Ile Ser Val Glu Met Lys Lys Glu Asp Phe Asp Ile Tyr
            20                  25                  30
Asp Glu Asp Glu Asn Gln Ser Pro Arg
        35                  40

<210> SEQ ID NO 23
<211> LENGTH: 238
<212> TYPE: PRT
<213> ORGANISM: artificial
<220> FEATURE:
<223> OTHER INFORMATION: GHBP

<400> SEQUENCE: 23

Phe Ser Gly Ser Glu Ala Thr Ala Ala Ile Leu Ser Arg Ala Pro Trp
1               5                   10                  15
Ser Leu Gln Ser Val Asn Pro Gly Leu Lys Thr Asn Ser Ser Lys Glu
            20                  25                  30
Pro Lys Phe Thr Lys Cys Arg Ser Pro Glu Arg Glu Thr Phe Ser Cys
        35                  40                  45
His Trp Thr Asp Glu Val His His Gly Thr Lys Asn Leu Gly Pro Ile
    50                  55                  60
Gln Leu Phe Tyr Thr Arg Arg Asn Thr Gln Glu Trp Thr Gln Glu Trp
```

```
                65                  70                  75                  80
Lys Glu Cys Pro Asp Tyr Val Ser Ala Gly Glu Asn Ser Cys Tyr Phe
                85                  90                  95

Asn Ser Ser Phe Thr Ser Ile Trp Ile Pro Tyr Cys Ile Lys Leu Thr
            100                 105                 110

Ser Asn Gly Gly Thr Val Asp Glu Lys Cys Phe Ser Val Asp Glu Ile
        115                 120                 125

Val Gln Pro Asp Pro Pro Ile Ala Leu Asn Trp Thr Leu Leu Asn Val
    130                 135                 140

Ser Leu Thr Gly Ile His Ala Asp Ile Gln Val Arg Trp Glu Ala Pro
145                 150                 155                 160

Arg Asn Ala Asp Ile Gln Lys Gly Trp Met Val Leu Glu Tyr Glu Leu
                165                 170                 175

Gln Tyr Lys Glu Val Asn Glu Thr Lys Trp Lys Met Met Asp Pro Ile
            180                 185                 190

Leu Thr Thr Ser Val Pro Val Tyr Ser Leu Lys Val Asp Lys Glu Tyr
        195                 200                 205

Glu Val Arg Val Arg Ser Lys Gln Arg Asn Ser Gly Asn Tyr Gly Glu
    210                 215                 220

Phe Ser Glu Val Leu Tyr Val Thr Leu Pro Gln Met Ser Gln
225                 230                 235

<210> SEQ ID NO 24
<211> LENGTH: 45
<212> TYPE: PRT
<213> ORGANISM: artificial
<220> FEATURE:
<223> OTHER INFORMATION: FIX298-342

<400> SEQUENCE: 24

Ile Phe Leu Lys Phe Gly Ser Gly Tyr Val Ser Gly Trp Ala Arg Val
1               5                   10                  15

Phe His Lys Gly Arg Ser Ala Leu Val Leu Gln Tyr Leu Arg Val Pro
            20                  25                  30

Leu Val Asp Arg Ala Thr Cys Leu Arg Ser Thr Lys Phe
        35                  40                  45

<210> SEQ ID NO 25
<211> LENGTH: 80
<212> TYPE: PRT
<213> ORGANISM: artificial
<220> FEATURE:
<223> OTHER INFORMATION: FIX47-125

<400> SEQUENCE: 25

Asp Asp Gly Asp Gln Cys Glu Ser Asn Pro Cys Leu Asn Gly Gly Ser
1               5                   10                  15

Cys Lys Asp Asp Ile Asn Ser Tyr Glu Cys Trp Cys Pro Phe Gly Phe
            20                  25                  30

Glu Gly Lys Asn Cys Glu Leu Asp Val Thr Cys Asn Ile Lys Asn Gly
        35                  40                  45

Arg Cys Glu Gln Phe Cys Lys Asn Ser Ala Asp Asn Lys Val Val Cys
    50                  55                  60

Ser Cys Thr Glu Gly Tyr Arg Leu Ala Glu Asn Gln Lys Ser Cys Glu
65                  70                  75                  80

<210> SEQ ID NO 26
<211> LENGTH: 272
```

<212> TYPE: PRT
<213> ORGANISM: artificial
<220> FEATURE:
<223> OTHER INFORMATION: vWF1-272

<400> SEQUENCE: 26

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

<210> SEQ ID NO 27
<211> LENGTH: 1390
<212> TYPE: PRT
<213> ORGANISM: homo sapiens

<400> SEQUENCE: 27

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys

-continued

```
            65                   70                  75                  80
Ile Gly Cys Asn Thr Cys Val Cys Arg Asp Arg Lys Trp Asn Cys Thr
                        85                  90                  95
Asp His Val Cys Asp Ala Thr Cys Ser Thr Ile Gly Met Ala His Tyr
                    100                 105                 110
Leu Thr Phe Asp Gly Leu Lys Tyr Leu Phe Pro Gly Glu Cys Gln Tyr
                115                 120                 125
Val Leu Val Gln Asp Tyr Cys Gly Ser Asn Pro Gly Thr Phe Arg Ile
            130                 135                 140
Leu Val Gly Asn Lys Gly Cys Ser His Pro Ser Val Lys Cys Lys Lys
145                 150                 155                 160
Arg Val Thr Ile Leu Val Glu Gly Gly Glu Ile Glu Leu Phe Asp Gly
                        165                 170                 175
Glu Val Asn Val Lys Arg Pro Met Lys Asp Glu Thr His Phe Glu Val
                    180                 185                 190
Val Glu Ser Gly Arg Tyr Ile Ile Leu Leu Leu Gly Lys Ala Leu Ser
                195                 200                 205
Val Val Trp Asp Arg His Leu Ser Ile Ser Val Val Leu Lys Gln Thr
            210                 215                 220
Tyr Gln Glu Lys Val Cys Gly Leu Cys Gly Asn Phe Asp Gly Ile Gln
225                 230                 235                 240
Asn Asn Asp Leu Thr Ser Ser Asn Leu Gln Val Glu Glu Asp Pro Val
                        245                 250                 255
Asp Phe Gly Asn Ser Trp Lys Val Ser Ser Gln Cys Ala Asp Thr Arg
                    260                 265                 270
Lys Val Pro Leu Asp Ser Ser Pro Ala Thr Cys His Asn Asn Ile Met
                275                 280                 285
Lys Gln Thr Met Val Asp Ser Ser Cys Arg Ile Leu Thr Ser Asp Val
            290                 295                 300
Phe Gln Asp Cys Asn Lys Leu Val Asp Pro Glu Pro Tyr Leu Asp Val
305                 310                 315                 320
Cys Ile Tyr Asp Thr Cys Ser Cys Glu Ser Ile Gly Asp Cys Ala Cys
                        325                 330                 335
Phe Cys Asp Thr Ile Ala Ala Tyr Ala His Val Cys Ala Gln His Gly
                    340                 345                 350
Lys Val Val Thr Trp Arg Thr Ala Thr Leu Cys Pro Gln Ser Cys Glu
                355                 360                 365
Glu Arg Asn Leu Arg Glu Asn Gly Tyr Glu Cys Glu Trp Arg Tyr Asn
            370                 375                 380
Ser Cys Ala Pro Ala Cys Gln Val Thr Cys Gln His Pro Glu Pro Leu
385                 390                 395                 400
Ala Cys Pro Val Gln Cys Val Glu Gly Cys His Ala His Cys Pro Pro
                        405                 410                 415
Gly Lys Ile Leu Asp Glu Leu Leu Gln Thr Cys Val Asp Pro Glu Asp
                    420                 425                 430
Cys Pro Val Cys Glu Val Ala Gly Arg Arg Phe Ala Ser Gly Lys Lys
                435                 440                 445
Val Thr Leu Asn Pro Ser Asp Pro Glu His Cys Gln Ile Cys His Cys
            450                 455                 460
Asp Val Val Asn Leu Thr Cys Glu Ala Cys Gln Glu Pro Gly Gly Leu
465                 470                 475                 480
Val Val Pro Pro Thr Asp Ala Pro Val Ser Pro Thr Thr Leu Tyr Val
                        485                 490                 495
```

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
            515                 520                 525

Glu Phe Glu Val Leu Lys Ala Phe Val Val Asp Met Met Glu Arg Leu
            530                 535                 540

Arg Ile Ser Gln Lys Trp Val Arg Val Ala Val Val Glu Tyr His Asp
545                 550                 555                 560

Gly Ser His Ala Tyr Ile Gly Leu Lys Asp Arg Lys Arg Pro Ser Glu
                565                 570                 575

Leu Arg Arg Ile Ala Ser Gln Val Lys Tyr Ala Gly Ser Gln Val Ala
            580                 585                 590

Ser Thr Ser Glu Val Leu Lys Tyr Thr Leu Phe Gln Ile Phe Ser Lys
            595                 600                 605

Ile Asp Arg Pro Glu Ala Ser Arg Ile Ala Leu Leu Leu Met Ala Ser
            610                 615                 620

Gln Glu Pro Gln Arg Met Ser Arg Asn Phe Val Arg Tyr Val Gln Gly
625                 630                 635                 640

Leu Lys Lys Lys Val Ile Val Ile Pro Val Gly Ile Gly Pro His
                645                 650                 655

Ala Asn Leu Lys Gln Ile Arg Leu Ile Glu Lys Gln Ala Pro Glu Asn
            660                 665                 670

Lys Ala Phe Val Leu Ser Ser Val Asp Glu Leu Glu Gln Gln Arg Asp
            675                 680                 685

Glu Ile Val Ser Tyr Leu Cys Asp Leu Ala Pro Glu Ala Pro Pro Pro
            690                 695                 700

Thr Leu Pro Pro Asp Met Ala Gln Val Thr Val Gly Pro Gly Leu Leu
705                 710                 715                 720

Gly Val Ser Thr Leu Gly Pro Lys Arg Asn Ser Met Val Leu Asp Val
                725                 730                 735

Ala Phe Val Leu Glu Gly Ser Asp Lys Ile Gly Glu Ala Asp Phe Asn
            740                 745                 750

Arg Ser Lys Glu Phe Met Glu Glu Val Ile Gln Arg Met Asp Val Gly
            755                 760                 765

Gln Asp Ser Ile His Val Thr Val Leu Gln Tyr Ser Tyr Met Val Thr
770                 775                 780

Val Glu Tyr Pro Phe Ser Glu Ala Gln Ser Lys Gly Asp Ile Leu Gln
785                 790                 795                 800

Arg Val Arg Glu Ile Arg Tyr Gln Gly Gly Asn Arg Thr Asn Thr Gly
                805                 810                 815

Leu Ala Leu Arg Tyr Leu Ser Asp His Ser Phe Leu Val Ser Gln Gly
            820                 825                 830

Asp Arg Glu Gln Ala Pro Asn Leu Val Tyr Met Val Thr Gly Asn Pro
            835                 840                 845

Ala Ser Asp Glu Ile Lys Arg Leu Pro Gly Asp Ile Gln Val Val Pro
            850                 855                 860

Ile Gly Val Gly Pro Asn Ala Asn Val Gln Glu Leu Glu Arg Ile Gly
865                 870                 875                 880

Trp Pro Asn Ala Pro Ile Leu Ile Gln Asp Phe Glu Thr Leu Pro Arg
                885                 890                 895

Glu Ala Pro Asp Leu Val Leu Gln Arg Cys Cys Ser Gly Glu Gly Leu
            900                 905                 910

-continued

Gln Ile Pro Thr Leu Ser Pro Ala Pro Asp Cys Ser Gln Pro Leu Asp
          915                 920                 925

Val Ile Leu Leu Leu Asp Gly Ser Ser Phe Pro Ala Ser Tyr Phe
    930                 935                 940

Asp Glu Met Lys Ser Phe Ala Lys Ala Phe Ile Ser Lys Ala Asn Ile
945                 950                 955                 960

Gly Pro Arg Leu Thr Gln Val Ser Val Leu Gln Tyr Gly Ser Ile Thr
              965                 970                 975

Thr Ile Asp Val Pro Trp Asn Val Val Pro Glu Lys Ala His Leu Leu
          980                 985                 990

Ser Leu Val Asp Val Met Gln Arg Glu Gly Gly Pro Ser Gln Ile Gly
          995                 1000                1005

Asp Ala Leu Gly Phe Ala Val Arg Tyr Leu Thr Ser Glu Met His
    1010                1015                1020

Gly Ala Arg Pro Gly Ala Ser Lys Ala Val Val Ile Leu Val Thr
    1025                1030                1035

Asp Val Ser Val Asp Ser Val Asp Ala Ala Asp Ala Ala Arg
    1040                1045                1050

Ser Asn Arg Val Thr Val Phe Pro Ile Gly Ile Gly Asp Arg Tyr
    1055                1060                1065

Asp Ala Ala Gln Leu Arg Ile Leu Ala Gly Pro Ala Gly Asp Ser
    1070                1075                1080

Asn Val Val Lys Leu Gln Arg Ile Glu Asp Leu Pro Thr Met Val
    1085                1090                1095

Thr Leu Gly Asn Ser Phe Leu His Lys Leu Cys Ser Gly Phe Val
    1100                1105                1110

Arg Ile Cys Met Asp Glu Asp Gly Asn Glu Lys Arg Pro Gly Asp
    1115                1120                1125

Val Trp Thr Leu Pro Asp Gln Cys His Thr Val Thr Cys Gln Pro
    1130                1135                1140

Asp Gly Gln Thr Leu Leu Lys Ser His Arg Val Asn Cys Asp Arg
    1145                1150                1155

Gly Leu Arg Pro Ser Cys Pro Asn Ser Gln Ser Pro Val Lys Val
    1160                1165                1170

Glu Glu Thr Cys Gly Cys Arg Trp Thr Cys Pro Cys Val Cys Thr
    1175                1180                1185

Gly Ser Ser Thr Arg His Ile Val Thr Phe Asp Gly Gln Asn Phe
    1190                1195                1200

Lys Leu Thr Gly Ser Cys Ser Tyr Val Leu Phe Gln Asn Lys Glu
    1205                1210                1215

Gln Asp Leu Glu Val Ile Leu His Asn Gly Ala Cys Ser Pro Gly
    1220                1225                1230

Ala Arg Gln Gly Cys Met Lys Ser Ile Glu Val Lys His Ser Ala
    1235                1240                1245

Leu Ser Val Glu Leu His Ser Asp Met Glu Val Thr Val Asn Gly
    1250                1255                1260

Arg Leu Val Ser Val Pro Tyr Val Gly Gly Asn Met Glu Val Asn
    1265                1270                1275

Val Tyr Gly Ala Ile Met His Glu Val Arg Phe Asn His Leu Gly
    1280                1285                1290

His Ile Phe Thr Phe Thr Pro Gln Asn Asn Glu Phe Gln Leu Gln
    1295                1300                1305

Leu Ser Pro Lys Thr Phe Ala Ser Lys Thr Tyr Gly Leu Cys Gly

```
                1310                1315                1320

Ile Cys Asp Glu Asn Gly Ala Asn Asp Phe Met Leu Arg Asp Gly
    1325                1330                1335

Thr Val Thr Thr Asp Trp Lys Thr Leu Val Gln Glu Trp Thr Val
    1340                1345                1350

Gln Arg Pro Gly Gln Thr Cys Gln Pro Ile Leu Glu Gln Cys
    1355                1360                1365

Leu Val Pro Asp Ser Ser His Cys Gln Val Leu Leu Pro Leu
    1370                1375                1380

Phe Ala Glu Cys His Lys Val
    1385                1390

<210> SEQ ID NO 28
<211> LENGTH: 220
<212> TYPE: PRT
<213> ORGANISM: artificial
<220> FEATURE:
<223> OTHER INFORMATION: vWF497-716-R545A

<400> SEQUENCE: 28

Glu Asp Ile Ser Glu Pro Pro Leu His Asp Phe Tyr Cys Ser Arg Leu
1               5                   10                  15

Leu Asp Leu Val Phe Leu Leu Asp Gly Ser Ser Arg Leu Ser Glu Ala
                20                  25                  30

Glu Phe Glu Val Leu Lys Ala Phe Val Val Asp Met Met Glu Arg Leu
            35                  40                  45

Ala Ile Ser Gln Lys Trp Val Arg Val Ala Val Val Glu Tyr His Asp
        50                  55                  60

Gly Ser His Ala Tyr Ile Gly Leu Lys Asp Arg Lys Arg Pro Ser Glu
65                  70                  75                  80

Leu Arg Arg Ile Ala Ser Gln Val Lys Tyr Ala Gly Ser Gln Val Ala
                85                  90                  95

Ser Thr Ser Glu Val Leu Lys Tyr Thr Leu Phe Gln Ile Phe Ser Lys
                100                 105                 110

Ile Asp Arg Pro Glu Ala Ser Arg Ile Ala Leu Leu Leu Met Ala Ser
            115                 120                 125

Gln Glu Pro Gln Arg Met Ser Arg Asn Phe Val Arg Tyr Val Gln Gly
        130                 135                 140

Leu Lys Lys Lys Lys Val Ile Val Ile Pro Val Gly Ile Gly Pro His
145                 150                 155                 160

Ala Asn Leu Lys Gln Ile Arg Leu Ile Glu Lys Gln Ala Pro Glu Asn
                165                 170                 175

Lys Ala Phe Val Leu Ser Ser Val Asp Glu Leu Glu Gln Gln Arg Asp
                180                 185                 190

Glu Ile Val Ser Tyr Leu Cys Asp Leu Ala Pro Glu Ala Pro Pro Pro
            195                 200                 205

Thr Leu Pro Pro Asp Met Ala Gln Val Thr Val Gly
        210                 215                 220

<210> SEQ ID NO 29
<211> LENGTH: 269
<212> TYPE: PRT
<213> ORGANISM: homo sapiens

<400> SEQUENCE: 29

Asn Pro Glu Leu Lys Asp Phe Asn Glu Glu Gln Leu Lys Cys Asp
1               5                   10                  15
```

Leu Glu Leu Asn Lys Leu Glu Asn Gln Ile Leu Met Leu Gly Lys Thr
            20                  25                  30

Phe Tyr Gln Asn Tyr Arg Asp Asp Val Glu Ser Leu Tyr Ser Lys Leu
        35                  40                  45

Asp Leu Ile Met Gly Tyr Lys Asp Glu Arg Ala Asn Lys Lys Ala
 50                  55                  60

Val Asn Lys Arg Met Leu Glu Asn Lys Lys Glu Asp Leu Glu Thr Ile
 65                  70                  75                  80

Ile Asp Glu Phe Phe Ser Asp Ile Asp Lys Thr Arg Pro Asn Asn Ile
                85                  90                  95

Pro Val Leu Glu Asp Glu Lys Gln Glu Glu Lys Asn His Lys Asn Met
            100                 105                 110

Ala Gln Leu Lys Ser Asp Thr Glu Ala Ala Lys Ser Asp Glu Ser Lys
            115                 120                 125

Arg Ser Lys Arg Ser Lys Arg Ser Leu Asn Thr Gln Asn His Lys Pro
130                 135                 140

Ala Ser Gln Glu Val Ser Glu Gln Gln Lys Ala Glu Tyr Asp Lys Arg
145                 150                 155                 160

Ala Glu Glu Arg Lys Ala Arg Phe Leu Asp Asn Gln Lys Ile Lys Lys
                165                 170                 175

Thr Pro Val Val Ser Leu Glu Tyr Asp Phe Glu His Lys Gln Arg Ile
            180                 185                 190

Asp Asn Glu Asn Asp Lys Lys Leu Val Val Ser Ala Pro Thr Lys Lys
            195                 200                 205

Pro Thr Ser Pro Thr Thr Tyr Thr Glu Thr Thr Gln Val Pro Met
            210                 215                 220

Pro Thr Val Glu Arg Gln Thr Gln Gln Ile Ile Tyr Asn Ala Pro
225                 230                 235                 240

Lys Gln Leu Ala Gly Leu Asn Gly Glu Ser His Asp Phe Thr Thr
                245                 250                 255

His Gln Ser Pro Thr Thr Ser Asn His Thr His Asn Asn
            260                 265

<210> SEQ ID NO 30
<211> LENGTH: 28
<212> TYPE: PRT
<213> ORGANISM: artificial
<220> FEATURE:
<223> OTHER INFORMATION: hCG C-terminus

<400> SEQUENCE: 30

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 31
<211> LENGTH: 50
<212> TYPE: PRT
<213> ORGANISM: artificial
<220> FEATURE:
<223> OTHER INFORMATION: F10AP

<400> SEQUENCE: 31

Ser Val Ala Gln Ala Thr Ser Ser Ser Gly Glu Ala Pro Asp Ser Ile
1               5                   10                  15

Thr Trp Lys Pro Tyr Asp Ala Ala Asp Leu Asp Pro Thr Glu Asn Pro

```
                20                  25                  30
Phe Asp Leu Leu Asp Phe Asn Gln Thr Gln Pro Glu Arg Gly Asp Asn
            35                  40                  45

Asn Leu
    50
```